US011263919B2

(12) United States Patent
Malhotra

(10) Patent No.: US 11,263,919 B2
(45) Date of Patent: Mar. 1, 2022

(54) FEEDBACK SIGNALS FROM IMAGE DATA OF ATHLETIC PERFORMANCE

(71) Applicant: NIKE, Inc., Beaverton, OR (US)

(72) Inventor: Vikram Malhotra, Portland, OR (US)

(73) Assignee: NIKE, Inc., Beaverton, OR (US)

(*) Notice: Subject to any disclaimer, the term of this patent is extended or adjusted under 35 U.S.C. 154(b) by 487 days.

(21) Appl. No.: 14/773,435

(22) PCT Filed: Mar. 11, 2014

(86) PCT No.: PCT/US2014/023313
§ 371 (c)(1),
(2) Date: Sep. 8, 2015

(87) PCT Pub. No.: WO2014/150457
PCT Pub. Date: Sep. 25, 2014

(65) Prior Publication Data
US 2016/0027325 A1    Jan. 28, 2016

Related U.S. Application Data

(60) Provisional application No. 61/793,472, filed on Mar. 15, 2013.

(51) Int. Cl.
G09B 19/00    (2006.01)
G06K 9/00    (2022.01)
(Continued)

(52) U.S. Cl.
CPC ........ *G09B 19/0038* (2013.01); *A61B 5/1038* (2013.01); *A61B 5/1127* (2013.01);
(Continued)

(58) Field of Classification Search
CPC ........ G09B 19/0038; G09B 5/02; G09B 5/04; A61B 5/1038; A61B 5/1127;
(Continued)

(56) References Cited

U.S. PATENT DOCUMENTS 4,289,307 A * 9/1981 Marshall, Jr ........... G10K 15/02
340/384.3
2001/0015123 A1* 8/2001 Nishitani ........... A63B 71/0686
84/615
(Continued)

FOREIGN PATENT DOCUMENTS

JP    2005270480 A    10/2005
JP    2005270534 A    10/2005
(Continued)

OTHER PUBLICATIONS

Pelletier, Jean-Marc, Sonified Motion Flow Fields as a Means of Musical Expression, Jun. 4, 2008,.*
(Continued)

Primary Examiner — James B Hull
(74) Attorney, Agent, or Firm — Banner & Witcoff, Ltd.

(57) ABSTRACT

Aspects of this disclosure relate to improving an athlete's ability to synchronize the movement of their body in time. Certain embodiments provide a feedback system that allows an athlete (or another individual, such as a trainer) to comprehend and optimize the timing of one or more components or features of an athletic movement. Image data, such as video, of an athlete performing physical activity may be utilized (alone or in combination with non-image data) may be used to generate and emit real-time feedback signals to provide an indication of tempo to the athlete. Still further aspects relate to using image and/or other sensor data to detect improper timing and/or movements of an athlete, and in response generating real-time feedback signals.

18 Claims, 10 Drawing Sheets

(51) Int. Cl.

| | | |
|---|---|---|
| *A61B 5/103* | (2006.01) | |
| *A61B 5/11* | (2006.01) | |
| *G16H 20/30* | (2018.01) | |
| *G16H 30/40* | (2018.01) | |
| *A63B 24/00* | (2006.01) | |
| *A63B 69/36* | (2006.01) | |
| *G09B 5/04* | (2006.01) | |
| *A61B 5/00* | (2006.01) | |

(52) U.S. Cl.
CPC ...... *A63B 24/0006* (2013.01); *A63B 24/0021* (2013.01); *A63B 69/36* (2013.01); *G06K 9/00342* (2013.01); *G09B 5/04* (2013.01); *G16H 20/30* (2018.01); *G16H 30/40* (2018.01); *A61B 5/0022* (2013.01); *A61B 5/0024* (2013.01); *A61B 5/1123* (2013.01); *A61B 5/681* (2013.01); *A61B 5/6807* (2013.01); *A61B 2503/10* (2013.01)

(58) Field of Classification Search
CPC ... A61B 5/0022; A61B 5/0024; A61B 5/1123; A61B 5/6807; A61B 5/681; G06F 19/3481; G06K 9/00342; A63B 24/0021; A63B 69/36
USPC .......................................................... 434/252
See application file for complete search history.

(56) References Cited

U.S. PATENT DOCUMENTS

| | | | | |
|---|---|---|---|---|
| 2006/0204045 A1* | 9/2006 | Antonucci | .......... | G06K 9/00342 |
| | | | | 382/107 |
| 2007/0060446 A1* | 3/2007 | Asukai | ............... | A63B 24/0021 |
| | | | | 482/8 |
| 2010/0130298 A1* | 5/2010 | Dugan | ............... | A63B 69/3623 |
| | | | | 473/223 |
| 2010/0199230 A1* | 8/2010 | Latta | ........................ | G06F 3/017 |
| | | | | 715/863 |
| 2010/0303289 A1* | 12/2010 | Polzin | ................ | G06K 9/00342 |
| | | | | 382/103 |
| 2011/0142303 A1* | 6/2011 | Mathew | ................. | G06K 9/342 |
| | | | | 382/128 |
| 2012/0242567 A1* | 9/2012 | Hsuan | .................... | A63H 37/00 |
| | | | | 345/156 |
| 2013/0002653 A1 | 1/2013 | Lee et al. | | |
| 2013/0029791 A1* | 1/2013 | Rose | .................. | G09B 19/0038 |
| | | | | 473/409 |
| 2013/0336577 A1* | 12/2013 | Lu | ............................ | G06K 9/00 |
| | | | | 382/154 |
| 2015/0255005 A1* | 9/2015 | Yoda | .................... | G09B 23/288 |
| | | | | 434/265 |

FOREIGN PATENT DOCUMENTS

| | | |
|---|---|---|
| JP | 2008528195 A | 7/2008 |
| JP | 2008529727 A | 8/2008 |
| JP | 2011120611 A | 6/2011 |
| WO | 2013002653 A1 | 1/2013 |

OTHER PUBLICATIONS

Boyd, Jeffrey, Godbout, Andrew; Multi-Dimensional Synchronization for Rhythmic Sonification, Jun. 18, 2012.*

Fermuller, Cornelia, Shulman, David, Aloimonos, Yiannis, The Statistics of Optical Flow, Dec. 6, 2000, Academic Press (Year: 2000).*

Jean-Marc Pelletier: "Sonified Motion Flow Fields as a Means of Musical Expression", 8th International Conference New Interfaces for Musical Expression, Jun. 5, 2008 (Jun. 5, 2008), pp. 1-6.

Jeffrey E Boyd et al: "Multi-Dimensional Synchronization for Rhythmic Sonification", Proceedings of the 18th International Conference on Auditory Display, Jun. 18, 2012 (Jun. 18, 2012), pp. 1-7.

Jordi Bolibar: Kinect Audio-Runner: Audio Feedback for Improving Performance Master Thesis, Dec. 31, 2012 (Dec. 31, 2012), pp. 1-64.

Andrew Godbout et al: "Corrective Sonic Feedback for Speed Skating: A Case Study", The 16th International Conference on Auditory Di splay (ICAD-2010), Jun. 9, 2010 (Jun. 9, 2010), pp. 1-8.

Jeffrey E Boyd et al: "In Situ Motion Capture of Speed Skating: Escaping the Treadmill", Computer and Robot Vision (CRV), 2012 Ninth Conference On, IEEE, May 28, 2012 (May 28, 2012), pp. 460-467.

International Search Report and Written Opinion—Patent Cooperation Treaty Application PCT/2014/023313—dated Sep. 22, 2014.

\* cited by examiner

FEEDBACK SIGNALS FROM IMAGE DATA OF ATHLETIC PERFORMANCE

CROSS REFERENCE TO RELATED APPLICATIONS

This application claims the benefit of U.S. Provisional Application Ser. No. 61/793,472, entitled "Feedback Signals from Image Data of Athletic Performance," filed Mar. 15, 2013, which application is incorporated by reference herein.

BACKGROUND

Athletes, both amateur and professional, often desire to improve their performance for a particular sport or athletic activity. In addition to improving physical prowess, athletes may see large sport-specific improvements with drills directed towards vision, reaction time, or other abilities. Improper use of equipment or devices may actually lower athletic performance. Similarly, incorrectly administering drills or routines can also prevent the athlete to be properly trained and/or lead to a false conclusion that an athlete is not performing to threshold level.

Many athletes and trainers, therefore, are often unable to accurately determine athletic attributes and performance levels of the athlete. This causes difficulty in training the athlete as well as accurately comparing the athlete's performance to others. Existing options include requiring the athlete to travel to a specific location (often hundreds of miles away) to a specific facility on a specific date to conduct a series of drills that will permit a more accurate determination of their abilities and performance level. Unfortunately, the athlete may not be able to afford the trip and/or be available on the specific date. Additionally, the athlete may have a sub-par performance on one day and thus be considered well-below their actual performance level. This often leads to athletes not attending these events, and as such, continue to misjudge their performance of specific activities and drills. Therefore, despite heavy training, the athlete may not be improving in the proper areas in an efficient manner.

Therefore, in view of the foregoing, improved systems and methods are desirable. Aspects of this disclosure are directed towards novel systems and methods that address one or more of these deficiencies. Further aspects relate to minimizing other shortcomings in the art.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure relate to system and methods configured to improve the athlete's ability to synchronize the movement of their body in time. Certain embodiments provide a feedback system that allows an athlete (or another individual, such as a trainer) to comprehend and optimize the timing of one or more components or features of an athletic movement. Certain aspects relate to providing feedback to an athlete regarding the athlete's performance of a physical activity. The feedback may be provided in real-time such that the athlete may obtain feedback during performance of the athletic activity. In accordance with one embodiment, image data of the athlete performing the athletic activity, or at least a portion thereof, may be obtained. In one embodiment, a plurality of sequential images during an athlete's performance of a physical activity may be obtained. The image data may be processed in real-time to identify the athlete performing a first feature of a first athletic movement. For example, the physical activity of swinging a golf club may have several movements, such as a backswing movement and a forward swing movement. Within each movement, several features may be identified.

One or more features of a movement may be detected from a motion parameter. For example, if the athletic movement is a backswing of a golf swing, then a feature of that backswing may be based on at least one of a velocity value, an acceleration value, a location of a body portion of the athlete, or a location of a sporting device within the image data. In certain embodiments, a determination of the motion parameter may be determined based upon, at least in part, that a velocity value or an acceleration value meets a first threshold. In certain embodiments, the motion parameter may be used to generate or alter the generated feedback signal. For example, an audible feedback signal may be modulated based upon the speed or acceleration of a baseball bat's motion.

Determining whether a feature has occurred may include determining whether one or more movements of objects represented by image data meet a threshold criterion. Exemplary criterion may include a movement criterion and a movement quality criterion. In one embodiment, a first criterion may serve as a filter that identifies certain images that may be of interest and the second criterion may further identifies what data within this group fits a more stringent criteria. In yet another embodiment, the first and second criteria may be independent. A first threshold may detect whether a first body portion moved. The selection and/or utilization of the one or more portions of the athlete's body represented within the image data may be based on the predetermined physical activity, user input, historical data, and combinations thereof among others.

One or more image capturing devices may capture images at different or variable frame rates. For example, an image capturing device may capture images at a variable rate between 50 to 100 frames per second (fps). Therefore, determinations of movement (and/or movement quality) may utilize rate of capture information to accurately determine time intervals between frames of data that may be separated by uneven periods of time.

In certain implementations, landmarks/distance calibrations may be utilized from time-stamped image data to allow for precise measuring of performance. For example, objects represented by image data may be utilized to determine whether movement thresholds are met. For example, markings on a field (such as yard lines) may be used to calibrate distance measurements. In certain embodiments, objects may be identified and upon identification, used in calibration processes. Such calibration techniques are not limited to stationary objects. In certain embodiments, the predetermined physical activity may be used (either in whole or in part) to select which body portion(s) are utilized and/or whether the movement of the portion(s)—as represented within the captured image data—meet a threshold. In certain embodiments, systems and methods may be implemented that utilize a different body portion based upon characteristics of the image data.

Further aspects relate to generating and transmitting a feedback signal in response to identifying the performance of the feature(s). The transmission may be in real-time. In certain embodiments, image data may indicate that the athlete is performing a second or additional features of a first athletic movement. Additional feedback signals, such as audible signals, may be based upon the movement properties of the second feature may be transmitted. In one implementation, the athlete receives audio feedback during performance of the athletic movement configured to provide audible tempo feedback in regards to the athlete's performance of the first and second features of the athletic activity. The audio feedback signal may include a first audible tone at a first frequency and a second audio feedback signal may be generated by modulating the audible tone to a second frequency. In yet other embodiments, visual and/or tactile feedback signals may be utilized.

Identification of features may comprise identifying an initiation image comprising: identifying pixels that correspond to at least one of a specific first body portion or sporting object, wherein the first body portion or sporting object is selected based upon a predetermined physical activity the athlete is to perform; and determining, based upon the identified pixels, whether the pixel data is altered between a plurality of images within the sequential images such that the alteration satisfies a first threshold. Processing image data may comprise the utilization of an optical flow process. An optical flow process may be provided as an input to a motion entropy determination process comprising: providing flow field data comprising a pixel-distance change of an identified object from a first image to a second image; and using the flow field data to identify a specific type of motion of the athlete represented in the image data during performance of the physical activity.

As one example of another embodiment, the physical activity may be a golf swing having an upswing athletic movement and a subsequent downswing athletic movement. Detecting image data that the athlete is performing the first feature may include detecting pixel data indicative that a golf club is within a first distance from a ground surface and determining that the second athlete is performing the second feature of the upswing athletic movement is detected from pixel data indicative that the golf club is within a second distance from a ground surface.

Further aspects relate to transmitting proper timing to the athlete based upon detecting a first and a second feature of the athletic movement. For example, based upon the detection of at least one of the first and the second feature, a feedback signal may be transmitted at a predetermined time. It may be based upon the occurrence of the first or second feature and be configured to indicate the proper timing for the athlete to perform an additional feature of the athletic performance.

A performance attribute of the athlete may be determined from the threshold information as well as other image-derived data. As one example, an initiation image (alone or in combination with another image) may be used to determine at least one performance attribute of the athlete. Example attributes may include, but are not limited to: speed, reaction, endurance, and combinations thereof.

Further aspects may be utilized to calculate an athletic rating of the user. In certain embodiments, a rating may be a sport-specific athletic rating. For example, a single athlete may have a different rating for football and running rating score.

These and other aspects of the embodiments are discussed in greater detail throughout this disclosure, including the accompanying drawings.

BRIEF DESCRIPTION OF THE DRAWINGS

The present disclosure is illustrated by way of example and not limited in the accompanying figures in which like reference numerals indicate similar elements and in which.

DETAILED DESCRIPTION

Aspects of this disclosure relate to determining athletic attributes of an athlete from image data. One or more determinations may be based alterations of image data between different images (or frames), such as alterations in pixels representing objects or portions of objects. Image data may be utilized to determine whether certain thresholds are met. Various threshold levels may be applied to one or more objects represented in the image data. In certain implementations, an athlete's performance of a physical activity, such as for example, a sprint or agility drill, or battery of field-based tests, may be analyzed according to image data. In certain implementations, landmarks/distance calibrations may be utilized from time-stamped image data to allow for precise measuring of performance (including, but not limited to: sprint or agility times, flight time for vertical jump, distance for throws). Data retrieved or derived from the image data may be used in scoring and/or ranking athletes. Such data may be used to provide training advice or regimes to the athletes or other individuals, such as coaches or trainers.

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

I. Example Personal Training System

A. Illustrative Computing Devices

Figure 1:
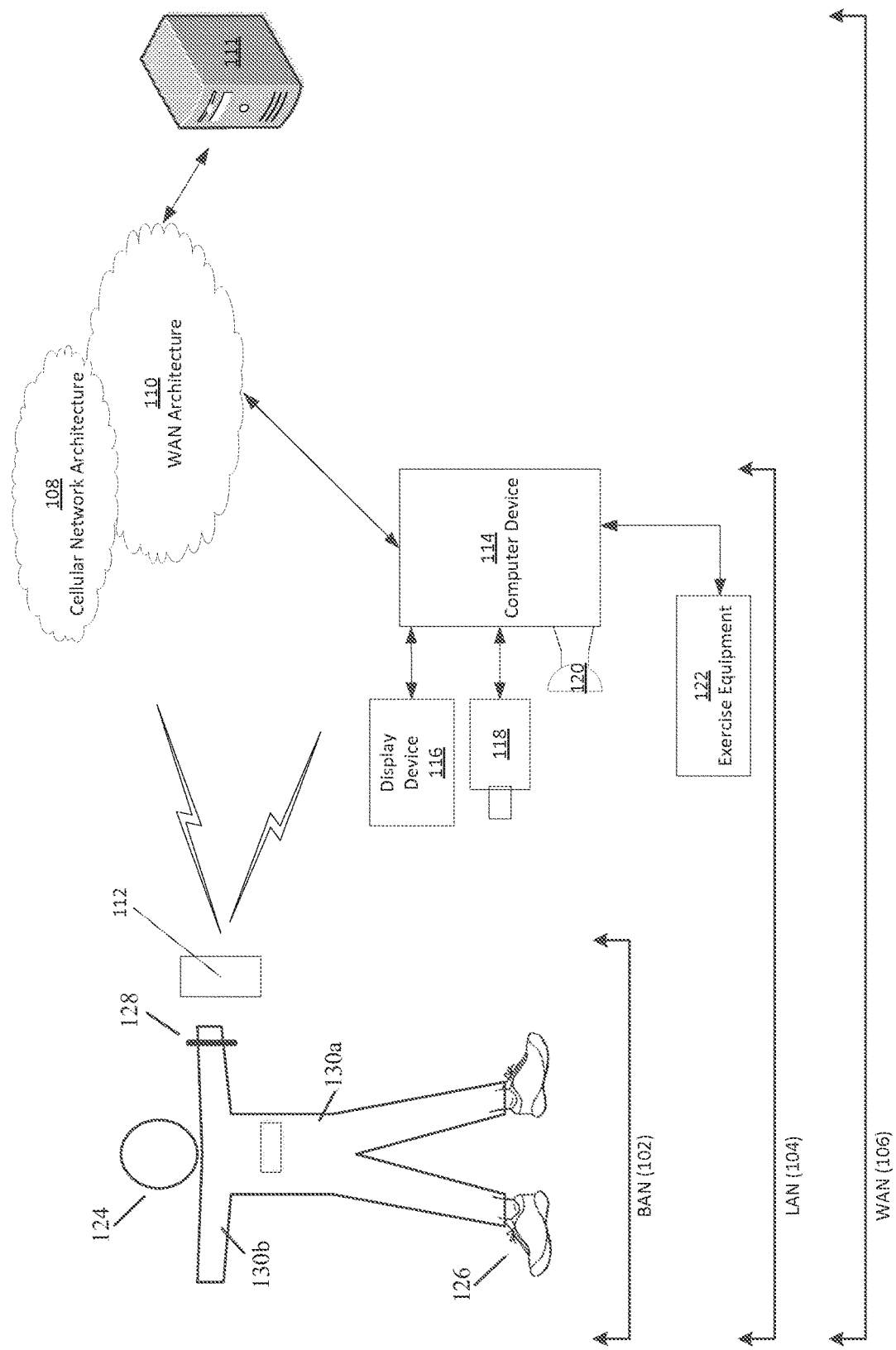
FIG. 1 illustrates an example of a system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), on or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® PlayStation, and/or a Nintendo® Wii gaming consoles. Those skilled in the art will appreciate that these are merely example devices for descriptive purposes and this disclosure is not limited to any console or computing device.

Figure 2:
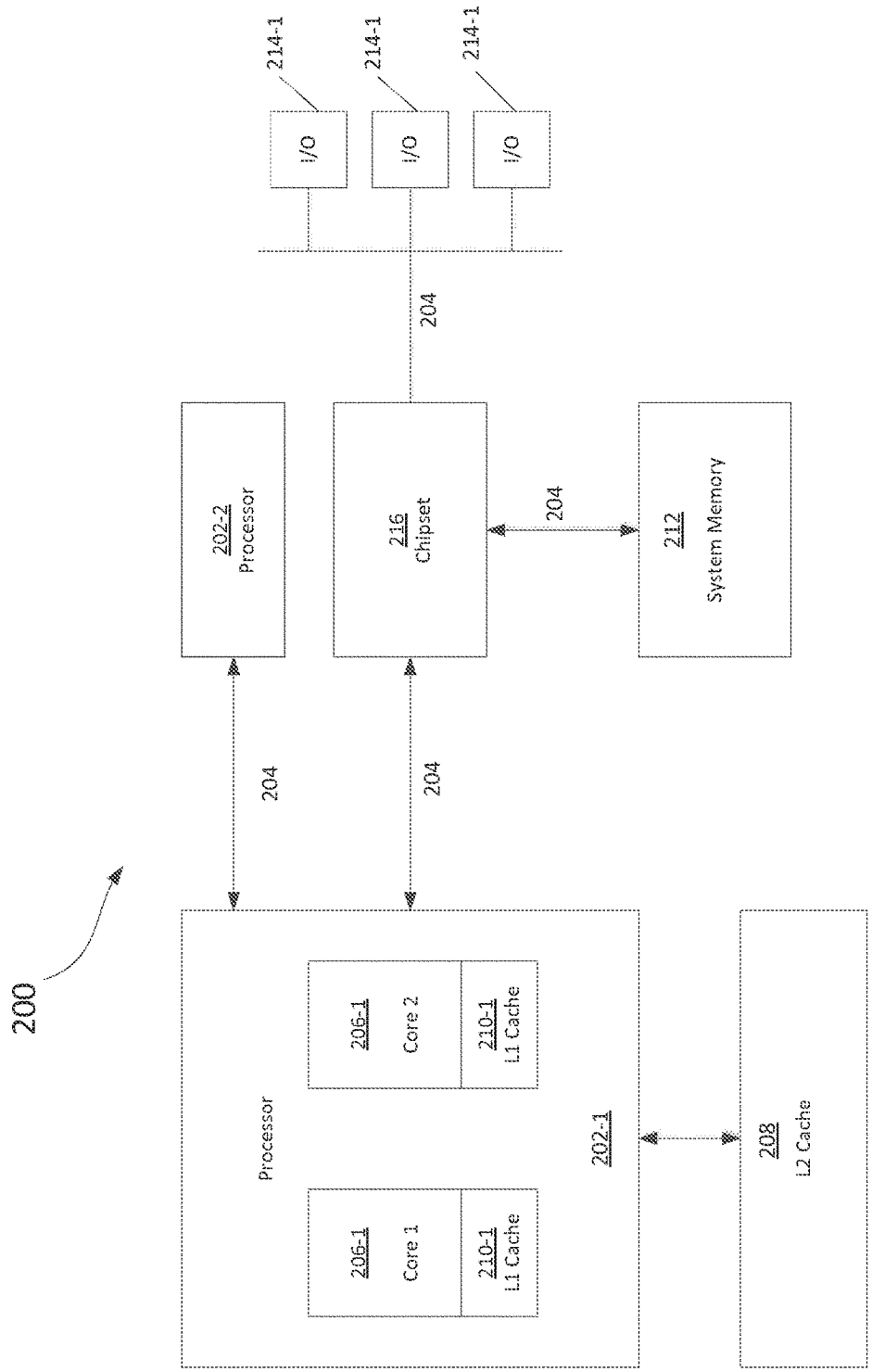
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise sever 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access points permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such one or more of the sensors discussed above in relation to FIGS. 1-3, that may provide information utilized, either independently or in conjunction with other sensors, such as one or more sensors associated with one or more structures. For example, a backboard may comprise a first sensors configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

B. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 102 and/or operate independently of computer device 102 (or any other device disclosed herein). For example, one or more devices in BAN 102 may be configured to function as an-all day activity monitor that measures activity regardless of the user's proximity or interactions with computer device 102. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
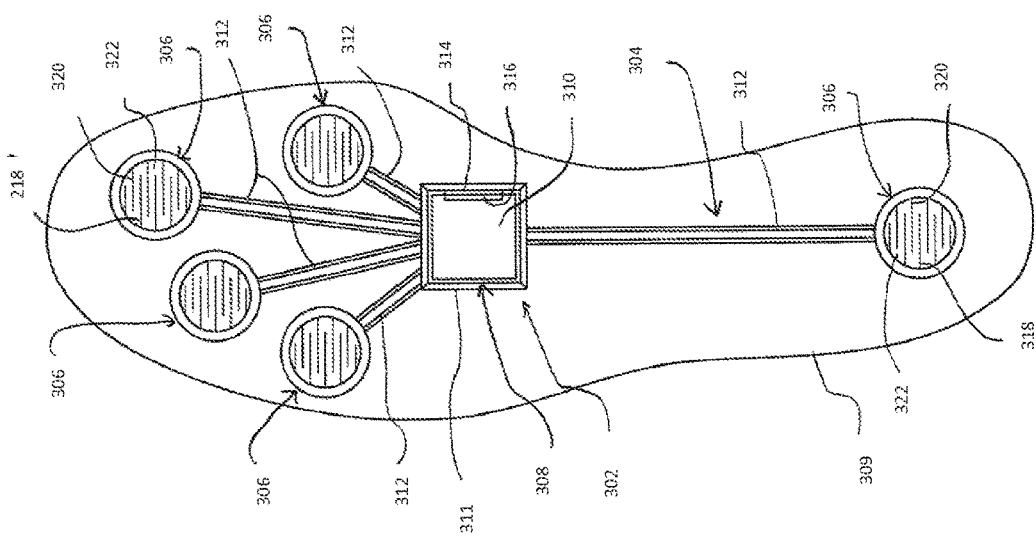
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 218, 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance" may be measured, which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
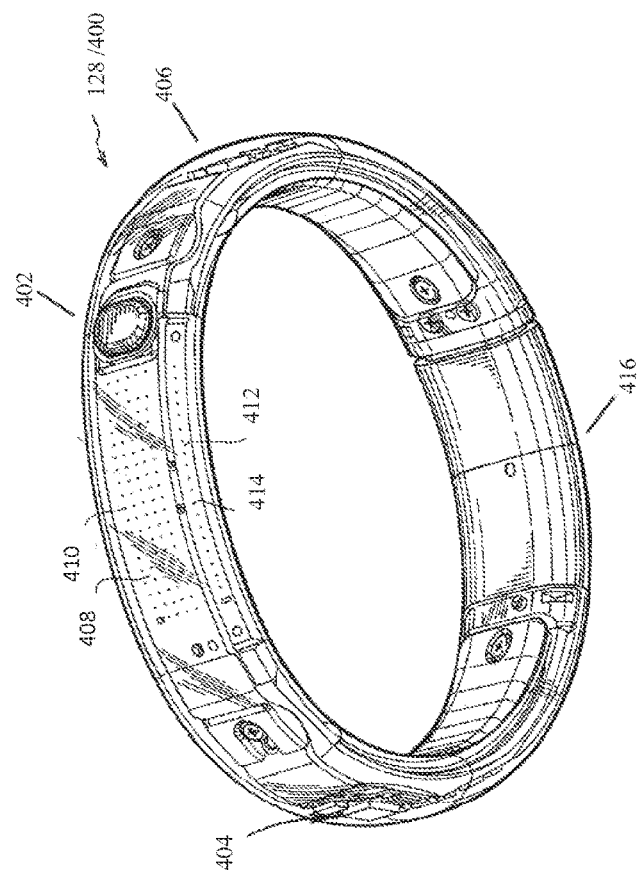
FIG. 4 shows another example sensor assembly that may be worn by a user in accordance with example embodiments.

As shown in FIG. 4, device 400 (which may resemble or comprise sensory device 128 shown in FIG. 1, may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
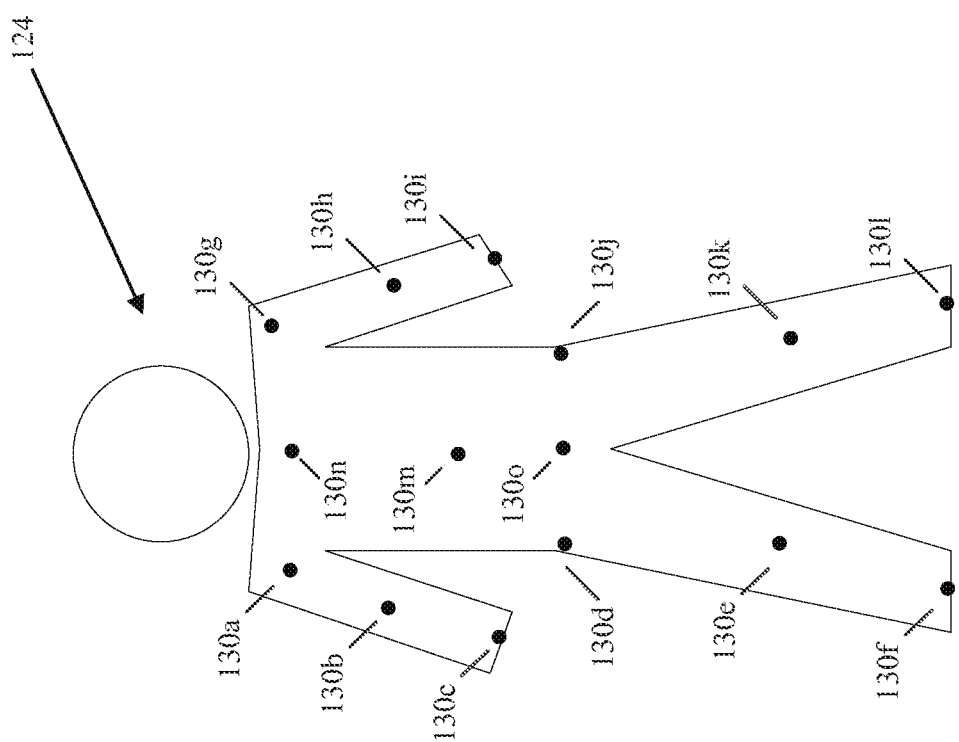
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-1306o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 1306f/130l with respect to one or more of location(s) 1306m-1306o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 146o may be located approximate to the naval of user 124. In certain embodiments, data from sensor locations 130m-130o may be utilized (alone or in combination with other data) to determine the center of gravity for user 124. In further embodiments, relationships between multiple several sensor locations, such as sensors 130m-130o, may be utilized in determining orientation of the user 124 and/or rotational forces, such as twisting of user's 124 torso. Further, one or more locations, such as location(s), may be utilized to as a center of moment location. For example, in one embodiment, one or more of location(s) 130m-130o may serve as a point for a center of moment location of user 124. In another embodiment, one or more locations may serve as a center of moment of specific body parts or regions.

II. Systems and Methods for Determining Athletic Attributes from Image Data

Aspects of this disclosure relate to system and methods configured to improve the athlete's ability to synchronize the movement of their body in time. Certain embodiments provide a feedback system that allows an athlete (or another individual, such as a trainer) to comprehend and optimize the timing of one or more components or features of an athletic movement.

Aspects of this disclosure relate to processing data taken while a user performs an athletic activity to determine athletic attributes. Image data, such as video, of an athlete performing physical activity may be utilized to generate and emit real-time feedback signals to provide an indication of tempo to the athlete. Further aspects relate to using data, including but not limited to image data and/or any sensor disclosed herein including those discussed in reference to FIG. 1, to generate emit real-time feedback signals alerting the athlete of proper timing of one or more features or component of an athletic movement. Still further aspects relate to using image and/or other sensor data to detect improper timing and/or movements of an athlete, and in response generating real-time feedback signals. These and other aspects will be discussed in the context of the following illustrative examples, which are meant to provide examples, but not limit, the scope of this disclosure.

Figure 6:
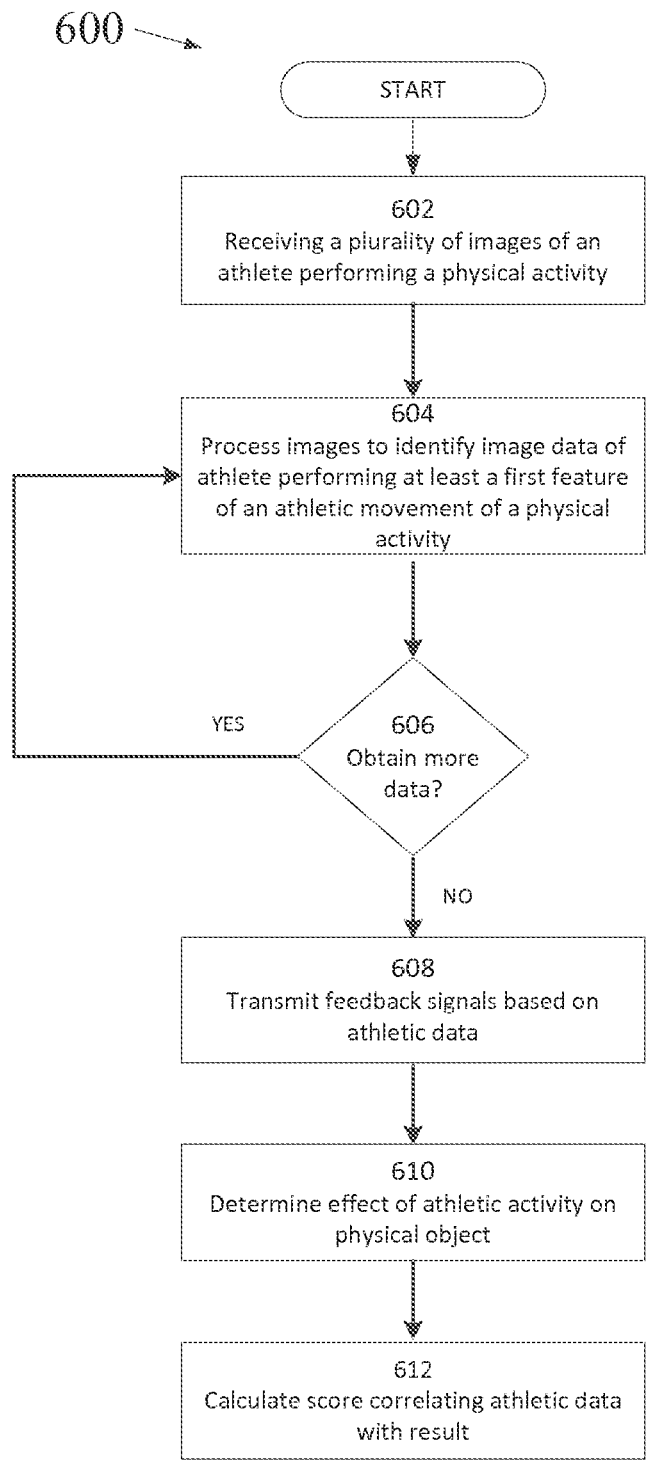
FIG. 6 is a flowchart of an example method that may be utilized to determine athletic attributes from image data in accordance with one exemplary embodiment.

FIG. 6 shows flowchart 600 of an example implementation that may be utilized in accordance with certain embodiments of this disclosure. One or more aspects of the methodologies provided as part of FIG. 6 or any other portion of this disclosure may be utilized to determine an athletic attribute of an individual. In certain embodiments, the tempo of one or more athletic movements may be determined. In this regard, one or more aspects of FIG. 6 may be used to provide a feedback system to allow an athlete to discern which tempo, power, speed, or other motion parameter during an athletic movement is correlated with superior results. Other aspects may be utilized to calculate an athletic rating of the user. In certain embodiments, a rating may be a sport-specific athletic rating. For example, a single athlete may have a different rating for golf and football. In further embodiments, the rating may be specific to a position or type of activity within the sport. For example, a first golf rating may relate to the tempo of a club swing while a second rating may relate to the tempo of a putter swing. As other examples, for a soccer rating, a first rating may be related to a forward position and a second rating may be related to a goalie position. For an American football rating, a first rating may relate to a quarterback position and the second rating may be for a running back position. Similarly, in the running sports, a first rating may be a sprint rating while another rating is related to longer distances.

Block 602 may be initiated to receive a plurality of sequential images of an athlete performing a physical activity. In one embodiment, the sequential images may be received in real-time. Those skilled in the art will appreciate that there may be inherent delays in receiving, storing, and/or processing the received data, even for "live" or real-time data. The physical activity may include any physical movement of the athlete, and be inclusive of the athlete's participation within a sport or activity with other participants. Those skilled in the art understand that most physical activities are not simple single movements. Instead, most activities include multiple athletic movements. As one example, a golf swing may be an athletic activity. A golf swing is known to require, at its simplest form, at least two distinct movements from the golfer: a backswing and a subsequent forward swing that makes contact with the golf ball. Further, a backswing movement is often not uniform but includes several distinct features, such as a starting point, an acceleration aspect as the club extends backwards, and the termination point, in which the forward swing begins. Similarly, a basketball jump shot comprises a plurality of movements, such as the athlete propelling off the court, bending of the elbows and movements of the wrist. Under different embodiments, each of these aspects of the jump shot may either be classified as a movement or a feature or component of a specific movement, nonetheless, it would beneficial to provide the athlete an indication of their tempo in regards to these aspects. Therefore, one or more embodiments encompass the reception of a plurality of sequential images comprising image data.

The image data may have been captured from an image capturing device, including any one or more of: a portable entertainment device, a stereoscopic camera, an infrared camera, a game console camera, and combinations thereof or other device known in the art, including but not limited to one or more of image capturing device 118, sensor, 120, computer device 114, and/or portable device 112 described in relation to FIG. 1. As discussed above, image data may be captured and/or received in real-time, such as to permit the athlete to obtain feedback during the performance of the athletic activity. In one embodiment, block 602 captures a plurality images wherein at least a first image comprises image data of an athlete before initiating performance of a predetermined physical activity and a plurality of subsequent images comprise image data of the athlete performing the predetermined physical activity. The image data may comprise pixel data.

In one embodiment, computer device 114 and/or device 112 may comprise an image capturing device (see, e.g., image capturing device 118 and sensor 120 shown in FIG. 1) and the trigger may be transmitted from at least one of a speaker, display, or light emitting device (e.g., display device 116 shown in FIG. 1 and/or display 408 of device 400 shown in FIG. 4), which may be directly connected to the device itself (such as being integral with the device or connected locally or via various network architecture (e.g., cellular network architecture 108 and/or WAN architecture 110). Yet other embodiments may comprise an electronic device, such as device 128 or computer device 114, configured to receive and/or decipher a trigger transmitted from a separate and distinct device, object or thing (including human-generated inputs, e.g., a human voice), such as via one or more sensing devices. In this regard, it is envisioned that the trigger of block 604 (and other triggers disclosed herein) may be machine-sensible with respect to at least one sensory input of one device in accordance with many different embodiments.

One or more embodiments may trigger the capturing of image data based upon a triggering event. Triggering events may be utilized to elicit an action from a user, such as to instruct an athlete to perform a physical action, such as shooting a jump shot, swinging a golf club or any other physical activity. In certain embodiments, triggering events may be utilized to elicit a portion of an action, such as performing just the backswing or the forward swing of a tennis racquet or other club, bat or other sporting device. As used herein, the term "sporting device" includes any physical object that may be used or implicated during a specific sport. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof. In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such one or more of the sensors discussed above in relation to FIGS. 1-5, that may provide information utilized, either independently, or in conjunction with, other sensors, such as one or more sensors associated with one or more structures. For example, a backboard may comprise a first sensors configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Sporting devices may comprise a removable sensor, such as an accelerometer module that is configured to detect acceleration. The accelerometer module may be replaced with a different sensor (i.e., pressure sensor). Using removable sensors may permit a sensor to be used with several different devices, such as soccer balls, powerballs, footballs, and/or allowing a user to upgrade or replace a faulty device, without having to obtain a new sensor. In certain embodiments, placement of one or more sensors 201 may be configured so that the weights of the included sensors do not change the balance or center of gravity of the sporting device.

In certain embodiments, one or more sensors may be held, attached or worn by a user. Exemplary "personal" devices may include, clothing such as shoes, shirts, shorts, gloves, hats, or electronic devices, such as watches, phones, and media players, among others. In one embodiment, sensors may be attachable to a user's shoe. In another embodiment, a device may be attachable to a user's arm, such as similarly performed by a watch, ring, or graspable by a hand, such as any handheld electronic device, including mobile terminal devices and/or personal media players. Those skilled in the art will readily appreciate, with the benefit of this disclosure, that one or more personal devices may comprise a sporting device, or any other component herein. Likewise, one or more structures may include or be configured to interact with one or more personal devices.

Figure 7:
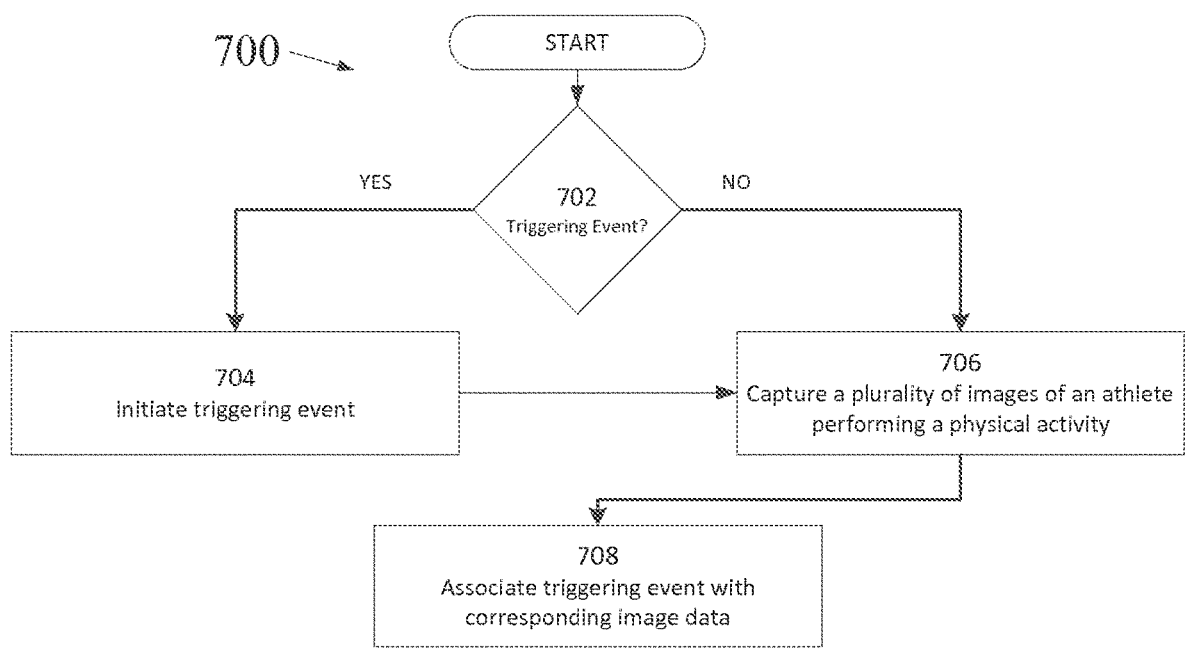
FIG. 7 is a flowchart showing an example implementation of utilizing a triggering event in accordance with one embodiment.

Triggering events may be utilized in triggering the capture of image data of an athlete performing the physical action. FIG. 7 provides an illustrative flowchart of one method that may be performed, such as part of block 602 of FIG. 6, or separate from block 602. Looking to FIG. 7, decision 702 may be implemented to determine whether to initiate a triggering event. The inputs to decision 702 or any other decision herein may be based on, inter alia, a user input, a sensor value, and combinations thereof. For example, in one embodiment, a triggering event may be configured to instruct or indicate to the athlete to initiate performance of a physical activity (see, e.g., block 704). Thus, whether to implement a triggering event and/or what trigger(s) may be utilized as part of the triggering event may depend on the physical activity, location of the trigger and/or user, a user input, predefined computer-executable instructions located on a non-transitory computer-readable medium, or combinations thereof. Although flowchart 700 is shown as beginning with decision 702, those skilled in the art will appreciate that flowchart 700 is not required to be initiated with decision 702 or any other decision. Further, decision 702 or any other decision or block disclosed herein may be implemented, either partially or in whole, before, after or during any other processes disclosed herein unless prohibited by the laws of nature.

A trigger (whether utilized in block 704 or any other process or system disclosed herein) may be audio, video, tactile, or combinations thereof. Indeed, those skilled in the art will appreciate that any human-sensible trigger may be utilized in accordance this disclosure. The trigger may indicate or instruct the user to perform a predefined physical activity. For example, a user may be instructed to initiate a 200 meter dash upon seeing a flash from an electronic device. In yet another embodiment, a user may be instructed to perform a drill specific to a certain sport upon hearing an audible cue. The trigger itself may provide instructions, yet in other embodiments; the user may be informed of what activity to conduct prior to receiving the trigger. In this regard, a simple flashing light or an audible noise may suffice in certain embodiments. In one embodiment, the human-sensible trigger is transmitted from a device operatively connected to a first camera that is configured to capture at least one image of the user performing the physical activity. Those skilled in the art will further realize that multiple triggers may be utilized within a single process.

At least one of a plurality of triggers may be of a different type than another trigger. For example, a first trigger may be an audible trigger and a second trigger may be a tactile trigger. As another example, a first trigger may be a first audible trigger and the second trigger may be a different audible trigger, such as by a different sound, pitch, volume, duration and/or combinations thereof. Further, different triggers may be implemented at different times and/or utilized to solicit different actions from the athlete. For example, a first trigger (such as implemented at block 704) may be configured to prompt the athlete to initiate performance of a first predetermined physical activity. In yet another embodiment, a second trigger may be implemented to instruct or cue the athlete to perform a second physical activity. A process similar or identical to block 704 may be implemented to implement the second trigger, including being based upon a decision (such as decision 702). In one example, to indicate to the athlete to perform a predefined movement during performance of the physical activity, a second trigger (which may resemble or be identical to the first trigger being implemented for a second instance) may be implemented to cue or instruct the athlete to perform a predefined movement during performance of the physical activity. Similarly, a trigger flag may be associated with a second image (or plurality of images). In one embodiment, second trigger flag may be with an image within the plurality of images that correlates to the timing of the second triggering event. One or more flags may be associated with the athlete's performance of activities responsive to the trigger(s). Such flags may be associated with images based upon perceived motions or actions determined from the pixel data. Exemplary methods of processing images are described herein, including but not limited to blocks 604 and 606 of FIG. 6 and 804 and 806 of FIG. 8. Those skilled in the art will appreciate other implementations are within the scope of this disclosure.

In certain embodiments, the capturing of image data (such as part of block 602 of FIG. 6, block 706 of FIG. 7, or any other process) may be responsive to a trigger (such as a trigger implemented as part of flowchart 700). For example, the trigger may be received or otherwise sensed by an electronic device. In one embodiment, an image-capturing device configured to capture image data of the athlete may detect, sense, and/or measure a trigger and, in response automatically initiate capturing images (See, e.g. block 706). In other embodiments, at least one image is captured before at least one triggering event. This may be useful, for example, to determine if a user "jumped" the trigger, such as in anticipation of a trigger. Regardless of whether image data is captured before or after the triggering event (e.g., block 706), a trigger flag may be associated with an image within the plurality of images (e.g. block 708). For example, a non-transitory computer-readable medium may comprise computer-executable instructions, that when executed by a processor, are configured to associate a trigger flag correlating with the timing of the triggering event with corresponding image data. Those skilled in the art will appreciate that there are many ways to flag or otherwise mark electronically stored image data; therefore, they are not explained in further detail here. As explained in more detail below, one or more trigger flags may be utilized in the determination of one or more athletic attributes.

Further aspects of this disclosure relate to processing image data, such as the image data captured as part of block

602. As discussed above, the capturing and/or receiving of the data may be conducted in real-time. Further embodiments also encompass the real-time processing of image data. As one example, block 604 may be initiated to process at least a portion of the plurality of images to identify image data of the first athlete performing a first feature of a first athletic movement during the physical activity. In certain embodiments, a location of a body portion of the athlete, or a location of a sporting device within the image data (absolute location or relative to another object, such as the athlete any other object represented by image data) may be used to detect the performance of one or more features of specific movements. For example, if the physical activity is a golf swing having an upswing athletic movement and a subsequent downswing athletic movement, an example detection may comprise detecting pixel data indicative that a golf club is within a first distance from a ground surface. In another embodiment, image data that the athlete is performing the second feature of the upswing athletic movement is detected from pixel data indicative that the golf club is within a second distance from a ground surface.

In yet other embodiments, an indication that a feature is being performed (or has been performed) may encompass the detection of a motion parameter. For example, at least one of a velocity value or an acceleration value may be utilized to determine initiation or occurrence of a feature (or indicate the likelihood that a feature will be occurring soon). Motion parameters may be determined entirely from the image data (such as, for example, determining pixel data changes between different images). In other implementations, motion parameters may be determined without using the image data. For example, one or more of the sensors described above in relation to FIGS. 1-5 may be utilized, alone or in combination with other sensors. In still yet further embodiments, one or more motion parameters may be determined from both image data and other sensor data. Those skilled in the art will readily appreciate that location, motion data, sensor data (both image and non-image based) may be used to detect the occurrence of a feature within an athletic movement (or the athletic movement itself).

Figure 8:
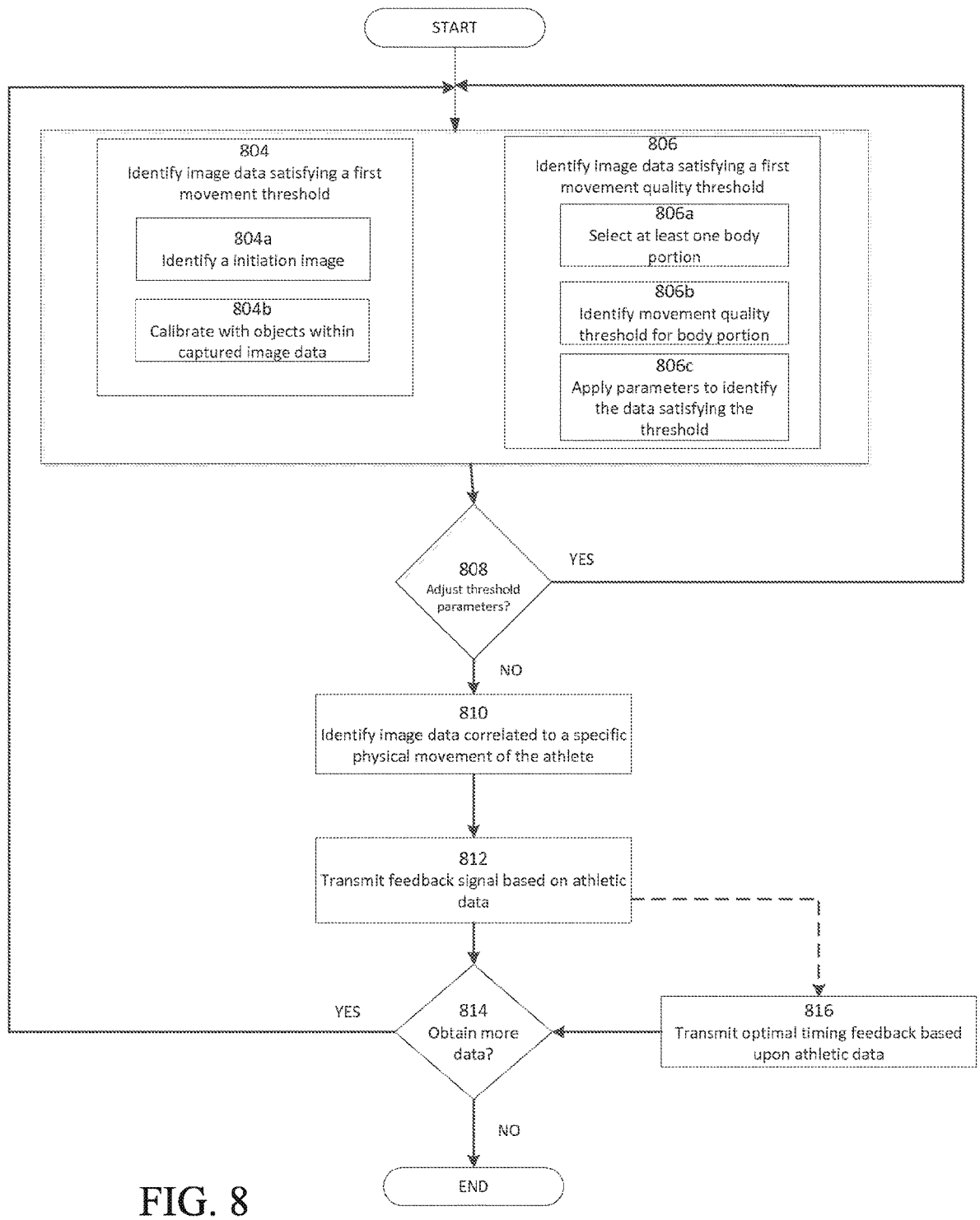
FIG. 8 is a flowchart showing an example implementation of transmitting a generating and transmitting feedback signals in accordance with one embodiment

FIG. 8 is a flowchart 800 of an example method that may be utilized to detect on or more features or athletic movements in accordance with certain embodiments. In certain embodiments, one or more elements of flowchart 800 may be implemented as part of block 604 of FIG. 6. In yet another embodiment, one or more elements of flowchart may be implemented entirely independent of block 604. In accordance with certain embodiments, image data may be processed to determine whether one or more movements of objects represented by image data meet a threshold criterion (See, e.g., block 804/806). Exemplary criterion may include a movement criterion and a movement quality criterion (See, e.g., block 804 and 806, respectively). In one embodiment, a first criterion, such as a first movement threshold criterion, may serve as a filter that identifies certain images that may be of interest and the second criteria further identifies what data (which may be within the same group) fits a more stringent criteria. The second criterion may be a movement quality threshold (See, e.g., block 612). In yet another embodiment, the first and second criteria may be conducted independently and in yet further embodiments, only one of a plurality of criteria may be utilized. In certain embodiments, criteria may include one or more movement threshold criterion, one or more threshold quality threshold criterion, and/or other criteria.

In one implementation, block 804 may be implemented and the outcome of block 804 may be used, at least in part, as a determination of whether to implement (or how to implement) block 806 or other process. In yet another embodiment, the first and second criteria may be conducted independently. For example, blocks 806 may be implemented simultaneously or at different times regardless of the outcome of each other. In yet further embodiments, only one of a plurality of criteria may be utilized. For example, only one of blocks 804 and 806 (or a portion thereof) may be implemented.

As one non-limiting example, block 804 may be implemented to process image data to identify data meeting a movement threshold. In one example, one or more of the plurality of received images may be utilized to identify a first range of images satisfying at least a first movement threshold. Image data (which may comprise whole or portions of images) may be analyzed to identify a first threshold level of movement of an object represented within the image data. The object may be a sporting device, such as a ball, bat, puck or glove. The object may also be the athlete or portion of the athlete. In certain embodiments, pixel data may be analyzed to identify a quantity of pixels in a portion of the captured images satisfying a first threshold level.

The threshold level may be configured to be indicative of a movement of an object. As non-limiting examples, one or more thresholds utilized as part of block 804 or any other process described herein may be tied to horizontal movement (e.g., running) or vertical movement (e.g., dunking a ball), or both. This threshold level can be entirely different than one or more additional threshold levels disclosed herein. For example, a first movement threshold may be triggered by the athlete's arm movement and a second threshold may pick specific movements tied to another body part or region, such as the other arm, a leg, etc. As another example, a first movement threshold may be associated with a golf club head while another is triggered by the athlete's arm movement. In one embodiment, the first threshold may detect whether a first body portion moved and/or whether a body portion moved along a specific axis. As used herein, a "body portion" may be any one or more sections, areas, systems, or portions of the user's body represented within image (e.g., pixel) data. In one embodiment, the image data may correlate to a single appendage (e.g., a leg or arm), group of appendages (e.g., an arm and leg or two arms), or portions thereof. In certain embodiments, the body portion may correspond to a portion of multiple appendages, such as the upper leg and/or inner arm areas, yet in other embodiments, the portion is devoid of appendages. In other embodiments, a first region (e.g., an upper region) may be distinguished from another region (e.g., a lower region). Those skilled in the art with the benefit of this disclosure will appreciate that any portion of the body represented by image data (such as at least one pixel) may serve as a "body portion" in accordance with certain embodiments. Further discussions of threshold levels will be discussed below, including with reference to movement quality thresholds in relation to block 806. Those discussions are incorporated herein and throughout this disclosure.

In one embodiment, at least a portion of the image data, such as a plurality of images or portions thereof, may be processed to identify an initiation image (see, e.g., block 804*a*). In one embodiment, the initiation image may be the frame or image in which a feature is first identified. In one embodiment, it may be an image in which the athlete first moves. In yet another embodiment, the initiation image may be the image in which a game or activity is initiated, regardless of whether the user moves. For example, in one embodiment, movement of another sprinter may signal the beginning of an event. In another embodiment, seeing a waving flag indicating an event has been initiated, or a gun emit smoke from being fired as well as other actions capturable by an image may be used to indicate an initiation image in accordance with various embodiments. In one embodiment, the first criterion may be directed towards movements associated with the specific athlete. In certain implementations, the initiation image is determined based upon a user input, such as a user selecting a UI element indicating the initiation image. For example, a user recording the athlete may want to flag an initiation image in real-time as the athlete is performing a specific action. For example, an image just prior to a basketball player attempting to dunk the ball may be identified as an initiation image. In certain embodiments, identification of the initiation image may result in capturing the image data at a different frame rate. Those skilled in the art will appreciate that other non-movement events may also be used in conjunction with certain embodiments. For example, one or more sounds, tactile inputs, or other information (including but not limited to those described above in relation to FIGS. 6 and 7) may be utilized in conjunction with one or more embodiments. A second movement threshold may be implemented to detect whether the movement met a threshold criterion.

In certain implementations, landmarks/distance calibrations may be utilized from time-stamped image data to allow for precise measuring of performance. For example, objects represented by image data may be utilized to determine whether movement thresholds are met (e.g., block 804*b*). For example, markings on a field (such as yard lines) may be used to calibrate distance measurements. In certain embodiments, objects may be identified and upon identification, used in calibration processes. For example, many sporting fields, tracks, courts, and the like have fixed dimensions. Likewise, basketball hoops, goalposts, goal nets, and other objects are often sized to specific known dimensions. These dimensions may be used to identify thresholds and/or determine whether certain thresholds have been met, including but not limited to: flight time for vertical jump, distance for throws, kick distance and power, among others, sprint times between two distances. Such calibration techniques are not limited to stationary objects. For example, balls, pucks, and other sporting devices may be used to calibrate distances. In this regard, a basketball has a known shape and size. Such dimensions may be used to calibrate measurements. Although these calibration techniques have been described in relation to block 604, those skilled in the art will appreciate that such techniques are not limited thereto, but instead may apply to any system and method described herein, including block 806. Further aspects of thresholds are described immediately below.

Certain systems and methods may comprise the utilization of decision 606 to determine whether additional data is required, such as whether multiple thresholds or criteria are met. For example, looking again to FIG. 8, block 806 of flowchart 800 may be implemented to determine whether image data (e.g., pixel data) satisfies another threshold, which may be unrelated to the movement threshold(s) of block 804. Thus, block 804 may be executed independently of block 806 and vise-versa. In certain embodiments, one or more processes of block 806 shown in FIG. 8 may be implemented in a parallel or serial fashion with respect to block 604 shown in FIG. 6. In one implementation, block 806 may identify a first body portion of the athlete that satisfies a first movement quality threshold. Further, it will be appreciated by those of skilled in the art that portions of various blocks, such as 804 and 806, may be implemented independently of other components. For example, sub-block 804*a* may be performed entirely separate from block 804. Further, it is to be understood that in alternative embodiments, one or more portions of blocks 804 and 806 (or any other block of FIG. 8) may be combined. For example, sub-block 804*a* may be utilized as part of block 806 and one or more of sub-blocks 806*a-c* may be utilized within block 804.

The selection and/or utilization of the one or more portions of the athlete's body represented within the image data may be based on the predetermined physical activity, user input, historical data, and combinations thereof among others. In one embodiment, block 806 may comprise one or more sub-parts that may be conducted independently of each other, yet in other embodiments may be at least partially dependent on another subpart of block 806 or another mechanism. For example, the predetermined physical activity may be used (either in whole or in part) to select which body portion(s) are utilized and/or whether the movement of the portion(s)—as represented within the captured image data—meet a quality threshold (see, e.g., blocks806*a* and 806*b*). As one example of identifying a body portion in block 806*a*, a first embodiment may utilize the image data associated with the athlete's legs, such as if the predetermined physical activity comprises or consists of a 200-meter sprinting event. Yet another embodiment may utilize image data associated with at least a portion of the athlete's legs as well as their arms. In yet further embodiments, a user input may be optionally provided to select which image data is utilized. A user input may be configured to select an option from a plurality of options, yet in other implementations a user may select any portion or part to be utilized.

Systems and methods may be implemented that utilize a different body portion or object represented within the image data based upon characteristics of the image data itself. For example, pixel data representing an athlete located at a first distance from the camera may be more accurate and/or precise than pixel data representing the same athlete located at a second distance that is further than the first distance with respect to a camera that captured the image data. Further, zooming, lighting conditions or other parameters may alter the quality of the captured image data as the athlete performs the athletic activity. Therefore, selecting a portion (e.g., 806*a*) and/or a quality threshold (e.g., 806*b*) may be based on a myriad of factors, some of which may be weighted more than others. In certain embodiments, selecting and/or switching which portion of the image data is utilized in one or more processing steps may be automatic, such that the athlete or operator of the camera does not have to make the selection. It may be performed in real-time, such that the selection and/or switching of objects represented in the image data as the data is being captured.

As another example, the athlete may travel throughout a 4-dimensional space during performance of the activity. Therefore, the camera(s) perspective of the athlete may be altered during the capture of the image data. In other embodiments, multiple cameras (which may have differing capabilities) may provide image data. These and other variables may result in different portions to be utilized or quality thresholds to be determined. For example, in one embodiment, image data comprising a sprinter running at a first distance may utilize, at the very least, image data comprising pixels representing the athlete's legs (or a portion thereof). However, as the user travels further away from the image capturing device, the number of pixels representing the athlete's legs (or portion thereof) may decline, therefore, in one embodiment, another body portion may be utilized to compensate for this reduction of pixel data. As one example, decision 808 may be implemented to determine whether to alter, update, switch or otherwise adjust the portion(s) of the athlete represented by pixel data utilized (e.g., block 806a) and/or how they are utilized (e.g., block 806b). In certain embodiments, block 806 may be implemented to determine whether to adjust parameters associated with a movement threshold of block 806 and/or block 806, and/or other thresholds.

For example, as a non-limiting example of adjusting one or more parameters of block 806, pixel data from an athlete's legs may be initially utilized, such as via block 806a, to identify image data for a first movement quality threshold; however, pixel data from the athlete's arms may supplement or replace the utilization of the pixel data representing the legs (such as via block 806a). Thus, in certain embodiments, the selection and switching of body portions or objects utilized may be an iterative process. Further, the threshold levels for one or more of these body "portions" may be altered based upon the quality of the image data for different images. In certain embodiments, a movement quality threshold may compare movement of multiple portions of the athlete's body and determine whether two or more portions move in relation to each other. For example, arm swing data may be compared with leg movement data to determine which most accurately reflects the predetermined physical activity.

In accordance with one embodiment, image data representing the relevant body portions (such as from block 806a) may be identified. Image data representing the relevant body portions may be isolated. In certain embodiments, surrounding pixel data may be utilized. Yet in other implementations, entire frames of image data may be utilized to determine if one or more threshold limits have been met. In certain implementations, an optical flow algorithm may be utilized to analyze the image data (e.g., pixel data) and determine movements of the body portions. In this regard, one or more image capturing devices may capture images at different or variable frame rates. For example, an image capturing device may capture images at a variable rate between 30 to 240 frames per second (fps). Therefore, determinations of movement may utilize rate of capture information to accurately determine time intervals between frames of data that may be separated by uneven periods of time. As another example, a first image capturing device may capture images at a rate of 100 fps and a second image capturing device may capture image data at a rate of 70 fps. Thus, data from these two image capturing devices may be normalized to account for variations in time between pixel movements. In one embodiment, at least a portion of the plurality of sequential images each represent about $\frac{1}{60}$th of a second, yet in another embodiment, at least a portion of the plurality of sequential images each represent no more than $\frac{1}{60}$th of a second. Because several frames of data may be captured and analyzed every second in some embodiments, real-time analysis can be provided to the athlete without substantial delay. In certain implementations, accurate time between an image having the first frame rate an image having the second time frame may be determined. This accurate time may be utilized in one or more processes. In certain embodiments, data from two images may be processed to determine movement between two frames of data. In one embodiment, pixel movement may be interpolated from two subsequent images. In certain embodiments, multiple cameras may be utilized. As one example, two cameras having the same frame rate may be configured to have a synchronized offset. Using a synchronized offset may allow a higher effective frame rate to be obtained. For example, if a first camera is set to 50 fps and captures images starting $\frac{1}{100}$th of a second before a second camera also set to 50 fps, then collectively, these images from these two cameras may be utilized to obtain an effective frame rate of 100 fps. Using multiple cameras may also be utilized to correct any incorrect data in accordance with certain embodiments. For example, a first camera configured to capture 50 fps may only capture 48 or 49 fps and thus data from a second camera may be used to provide accurate image data during the relevant time period.

Using the identified parameters, image data (e.g., pixel data) is utilized to determine that a first body portion movement quality threshold is met (see, e.g., block 806c). In one embodiment, image data representing the human form may be utilized to identify pixels or other image data representing the athlete. If multiple athletes are present within the frames, the specific athlete of interest may be isolated. In one embodiment, the athlete may be isolated based upon known parameters of the athlete (e.g., height, weight, color of clothing). In another embodiment, a user input may indicate which pixel data represents the athlete. In yet further embodiments, the athlete may wear a detectable marker configured to be detectable by at least one electronic device. Those skilled in the art will readily understand that these are merely examples.

Certain implementations may weigh one or more parameters resulting from the optical flow algorithm or other processes utilized to determine image data movement, such as movement of pixels. In this regard, aspects of this disclosure relate to novel motion entropy algorithms In certain embodiments, data from pixel movements between a plurality of images may be utilized to identify types of motion. As one example, data provided or derived from an optical flow process may be used. Example data may include the pixel-distance change of an identified object from one frame or image to another frame or image (sometimes referred to in the art as the "flow field"). These may be utilized in parameters that identify specific types of motion. In certain embodiments, these outputs may be used for segmentation and motion identification. In one embodiment, large-scale motion may first be identified and more detailed motions may then be identified. As an example, a first process may determine that an athlete is running and, in response, one or more processes may then be used to specifically detect hand motion and characterize that. Other motions that may be identified or derived include: initiation of the activity, acceleration, velocity, reaction, tempo, distance travelled by an object, or completion of the activity. Further embodiments may utilize one or more processes to determine which of segmentation, scaling, or other features may be implemented, or the extent they are utilized.

These or other processes may be used to provide an output concluding that a particular motion was occurring at the respective frame(s). In one embodiment, an athletic movement (or feature of a movement) may be detected from a motion parameter based on at least one of a velocity value, an acceleration value, a location of a body portion of the athlete, or a location of a sporting device within the image data. Determinations that a threshold is met may be based, at least in part, on the motion parameter. For example, the determination of the motion parameter is determined based upon, at least in part, determining that a velocity value or an acceleration value meets a first threshold. One or more of these attributes may be determined entirely from the image data. However, as discussed above, other sensor data may be used, either independently or in conjunction with image data.

In this regard, aspects of this disclosure relate to identifying image data (such as but not limited to specific images) that correlate to a specific physical movement or activity of the athlete (e.g., block 810). For example, certain embodiments may detect initiation of the athletic activity, performance of an athletic movement, and/or the occurrence of a movement feature. As non-limiting examples, image data may be used to identify one or more actions, including: initiation of the activity, levels of acceleration, velocity, reaction, and/or tempo, distance travelled by an object, completion of the activity, among others. As discussed above, objects (either stationary or in motion) may be utilized to calibrate measurements, including those relating to movement quality thresholds.

Thus, block 810 may be implemented to identify image data (including specific frames or images) such as including, but not limited to: an initiation image, a termination image, or any other image comprising motion data that can be identified based upon the systems or methods disclosed herein. An initiation image and/or a termination image may be identified for one or more athletic movements, athletic features of a movement, or combinations thereof. As one example of an embodiment that utilizes blocks 806 and 810, block 806 may be utilized to determine whether pixel data is altered between two subsequent images such that the alteration satisfies a specific first body portion (e.g., upper arm) movement quality threshold. As described above, image data between two successive images may be interpolated or otherwise derived from existing image data. Thus, based upon the first body portion quality threshold being met, the respective image in which it first occurred may be identified or flagged as an initiation image. In one embodiment, an implementation of block 810 may utilize subsequent images following what may be deemed an initiation image in any athletic determinations. For example, if analysis of a plurality of subsequent frames further reveal that the athlete is engaged in a specific activity, then one embodiment may analyze past frames (or portions thereof) to identify where the specific action began. Because multiple frames may be captured within a second, certain embodiments may analyze tens of images without undue delay. Yet in other embodiments, systems and methods may identify the initiation image (or other image) based solely on that image and/or images preceding that image. Similarly, a termination image may be identified based upon a certain threshold (or plurality of thresholds) not being met. In other embodiments, a termination image may be identified based on a second threshold being met, such as for example a different body portion movement quality threshold. In accordance with one embodiment, movement of an athlete's torso may be used as identification of an initiation image (e.g., block 804a) of a baseball player pitching a ball, while a movement quality threshold relating to the quality of movement of the athlete's throwing arm may be used to determine that the athlete is pitching the ball and/or released the ball (e.g., block 806). In certain embodiments, image data indicating that the ball struck a catcher's mitt or a bat may signify the termination image of the pitch. Other thresholds, however, such as, but not limited to, one described in block 804 may also be utilized, either alone or in combination, with a body movement quality threshold.

Thus, image data, alone or in combination with other sensor data, may be utilized to identify a performance attribute of the athlete. As one example, an initiation image of a feature (alone or in combination with another image) may be used to determine at least one performance attribute of the athlete. Example attributes may include, but are not limited to: speed, reaction, endurance, and combinations thereof. In another embodiment, a completion image comprising image data of the athlete completing the feature (which may be identified at block 810 from data obtained at one or more processes of block(s) 804 and/or 806 may be utilized. In one implementation, physical activity duration based upon the initiation image and the completion image may be calculated. Such information may be used to determine velocity, acceleration, tempo, pace, or a combination thereof. As will be explained below, such information may also be used in one or more calculations relating to a performance rating.

Determinations of an attribute may utilize data obtained from one or more other sensors that are not used to capture the image data. In accordance with certain embodiments, alterations of the image data responsive to external stimuli may be considered. In one embodiment, flagged images associated with triggering events may be utilized. As one example, a reaction value for the athlete may be determined based upon the duration of time between the image associated with a trigger flag and the initiation image. For example, an external stimulus, such as an audible or visual cue, may indicate the start of a race and accordingly, the associated image(s) may be flagged as being correlated to a first triggering event (e.g., block 708). Based upon one or more thresholds being met, such as described herein (e.g., blocks 804 and 806), it may be determined that a user has initiated a predetermined activity. In certain embodiments, the activity may be a sport-specific activity. Thus, the user's reaction time may be determined from the flagged image of the triggering event and the initiation image.

As discussed above in relation to block 704, one or more triggering events may occur before, during or after the athlete's performance of the physical activity. In one embodiment, a second triggering event may be utilized to indicate to the athlete to perform a predefined movement during performance of the physical activity. A second trigger flag may be associated with an image that correlates to the timing of the second triggering event (such as block 708 or another process). Another flag may be associated with an image correlated to the athlete performing the predefined movement. In one such embodiment, a second reaction value for the athlete based upon the duration between an image associated with the second trigger flag and an image correlated with the athlete performing the movement may be calculated.

In further embodiments, sensor data (inclusive of non-image sensor data) may be utilized in any determinations, derivations or calculations described herein. Sensor data may be captured from sensors including, but not limited to: a wrist-worn sensor, a footwear-worn sensor, a portable entertainment electronic device, and combinations thereof. In accordance with one embodiment, sensor data may be utilized to conduct image stabilization upon at least a portion of the plurality of images. In one implementation, sensor data may be received from a sensor operatively attached to the athlete and used for image stabilization, identification of the athlete from an plurality of objects within the captured image data, determinations of when to capture images, determinations of what image data to process, and/or other utilizations.

Further aspects of this disclosure relate to transmitting feedback signals to the athlete (e.g., block 608 of FIG. 6). The feedback signals may be based on the detected athletic data and/or optimal timing for certain athletic movements based upon the athletic data. As used herein, a feedback signal may be audio, visual, and/or tactile, such as a vibrating or pulsing tactile device, an optical device (e.g. LED or other light) that blinks, changes color, alters brightness, etc., an audio device that may emit a sound, such as ticks, beeps, and/or music or other audio effects that may contain rhythmic properties, be continuous, sequential, and/or exhibit other properties. As non-limiting examples, certain embodiments may utilize electroactive polymers (EAPs) that provide haptic feedback and/or vibration motors. In certain embodiments, one or more feedback devices may be worn on (or otherwise in contact with (directly or indirectly) with the body. The feedback may be adjustable and/or controllable.

Using flowchart 800 of FIG. 8 as one example, block 812 may be implemented to transmit a real-time feedback signal to the athlete. The feedback may be transmitted in response to identifying the performance of an activity (e.g., swinging a club), movement of an activity (e.g., the backswing) or feature of a specific movement (e.g., initiating the backswing, or speed/location of the club during a backswing, or combinations thereof. For example, in one embodiment, determination that a threshold was met or position for the body or equipment was reached (such as part of block 702) and/or that image data was correlated to a specific movement (such as part of block 810), may result in a determination that a first feature of a backswing is or has just occurred. As one example, the position of some part of the body, or the position/3D orientation of the equipment in use, if any, could be a trigger for the feature determination. Based upon the determination, a feedback signal, such as an audible tone, may be transmitted to the athlete.

Many athletes will desire to know more than just a single data point (such as when a feature is initiated or ended). In this regard, using multiple data points may be more beneficial in many instances. Using multiple data points, such as for example, detecting multiple features with a movement) and transmitting feedback to the athlete that allows distinction between the different features may be greatly beneficial. For example, one aspect that can greatly affect a golf swing (or any other action such as a tennis swing) is the speed of the swing itself. Swings that are too slow can result in less energy transfer to the ball, and swings that are too fast may cause the golfer to lose control and consistency in the swing. The "tempo" of the swing, or in other words the timing of the backswing and forward swing, can also have a profound effect on the speed and consistency of the swing, as well as other aspects of the swing.

Therefore, block 812 may be initiated (or repeated based upon image data) to transmit an audio feedback tone at various frequencies to provide feedback on the tempo of the golf swing. For example, decision 814 may be implemented to cause the transmission of multiple feedback signals that are based upon real-time data. In certain embodiments, previously recorded data may be analyzed. Image data may detect features (e.g., based upon speed, acceleration, and/or location of the club during a backswing), and as a result, different tones (or frequencies of the tone) may be transmitted to provide an indication of tempo. Different athletes may have different optimum swing tempos. Thus, providing a generic tempo to mimic may not assist the athlete. In this regard, a single golfer may even have different optimum swing tempos for different clubs. For example, a golfer may have one optimum swing tempo for a driver or other wood club, another for long irons, another for short irons, and another for putting. However, it can be difficult for a golfer to determine his/her optimum swing tempo(s), and it can additionally be difficult for a golfer to maintain the optimum swing tempo(s) during practice and/or play.

Rather than attempting to fit every athlete into a one-size-fits-all approach, providing real-time feedback based upon, at least in part, image data of the athlete's own performance more readily allows the athlete to improve. For example, in certain embodiments, after sending a first audio feedback signal (or any other type of feedback signal) in real-time based upon detection of a first feature, a second audio feedback signal based upon the movement properties of a second feature may be transmitted, such that the athlete receives audio feedback during performance of the athletic movement configured to provide audible tempo feedback in regards to the athlete's performance of the first and second features of the athletic activity.

In this regard, example embodiments contemplate capturing movement associated with an activity (e.g., constituent movements and/or one or more components thereof) via video or image sequences to obtain image data, analyze that image data, which analyzed data is an input to a function that translates the analyzed data to feedback provided to the user. The feedback is directed to enable the user to "groove" their movement(s) in an activity, e.g., to groove their own swing. To "groove" implicates that the user is, generally, neither seeking to duplicate the movement(s) (e.g., swing) of another participant (e.g., a pro) nor necessarily seeking to attain some theoretical or ideal movement (e.g., such ideal may simply not be physiologically attainable for such user). Rather, the user is seeking to find and internalize the movement(s) (e.g., a swing) that is natural to themselves, including enabling consistent reproduction of the "grooved" movement(s). The grooved movement may be time bound, i.e., applicable as to the user's current circumstances.

Those skilled in the art will appreciate that the feedback signal may be transmitted by any electrical, mechanical, or electro-mechanical device. In one embodiment, an electronic device that includes a memory storing computer-executable instructions and a processor in communication with the memory, such as described in relation to FIGS. 1-4 may be utilized. A processor may be configured to execute computer-executable instructions on a non-transitory computer-readable medium to perform a number of actions. The device (e.g. the processor) may receive an input of a specified feedback signal or signals (e.g., a plurality of audio signals as the data is analyzed) and identify an audio tone or file for the feedback signal(s). Thus, in certain embodiments, a plurality of tones exhibit a tempo that is correlated to a tempo of the athlete's movement. Thus, certain aspects relate to a tempo indicating device for providing the feedback signal. The tempo indicating device may include an input for receiving information to output, an output configured to emit one or more different types of feedback signals.

In one embodiment, a tempo indicating device may be any device that is configurable to emit a sequence of regular, metrical beats to a user, also referred to as a rhythm, in a format that is recognizable to the user. For example, the format for emitting the rhythm may include: audio, visual, and/or tactile, such as a vibrating or pulsing tactile device, an optical device (e.g. LED or other light) that blinks, changes color, etc., an audio device that may emit a rhythmic sound, such as ticks, beeps, etc., or music or other audio effects that may contain rhythmic properties. The tempo indicating device may be adjustable and/or controllable to change the tempo (i.e. beat frequency) of the rhythm that is emitted to the user, such as based upon the detected athletic data. As one example, a first audio feedback signal may be a first audible tone at a first frequency and systems and methods may be employed for generating the second audio feedback signal by modulating the audible tone to a second frequency.

Further aspects of this disclosure relate to providing feedback regarding proper or optimal timing of events based upon detected athletic activity data (see, e.g., 816). For example, one or more of the above-mentioned systems and methods may be used to first identify aspects of the athlete's activities. Using a golf swing as an example, image processing methodologies (alone or in combination with data from non-image based sensors) may be used to detect the timing and/or tempo of the athlete's backswing and/or forward swing. In this regard, example embodiments contemplate capturing, during the activity, constituent and/or components (e.g., a golf swing), data from wearable sensors, such data being employed in a "sensor fusion" (e.g., to provide synergistic features/functionality) so as to enhance analysis of the acquired data (e.g., image data) and, in turn, enhance the feedback to the user (e.g., by more accurate or beneficial audio feedback).

Feedback systems may be implemented to provide feedback signals to the athlete as discussed above, such as to indicate the tempo of the golf swing. However, in additional embodiments, based upon the detection one or more features of the backswing or forward swing, an additional feedback signal may be transmitted at a predetermined time configured to indicate the proper timing for the athlete to perform an additional feature of the athletic performance, such as making contact with the ball. The transmission and/or attributes of the additional "optimal timing" feedback signal may be based upon the occurrence of one or more features of a movement. In certain embodiments, features of a backswing may be utilized to determine when (or even whether) to transmit the additional feedback signal of the additional feature (e.g., making contact with the ball). Thus, an athlete may receive feedback, such as various audible tones) indicative of the tempo of their backswing and their forward swing, and despite the tempo of the forward swing, an additional feedback signal may mark the timing of an optimal point in time to make contact with the ball, based upon properties the detected backswing. Yet, other embodiments may use data relating to multiple features from different movements (e.g., both a backswing and the forward swing). Thus, certain embodiments may not only provide feedback of the user's current athletic movement, but also feedback based upon proper and/or accurate timing events in view of the current athletic movements.

As discussed herein, feedback generation systems and methods may include audio feedback. In one example, one or more tones may be assigned with output data associated with a plurality of swing features. The tones may be assigned using any of various schema. As an example, an assignable tone may be associated with one or more velocities, accelerations, rotations, etc. associated with a feature. For example, each tone assignment may be based solely on one of a velocity, an acceleration, or a rotation. Alternatively, each tone assignment may be based on a combination of one or more of these, or other combinations.

As another example, each of a plurality of image or video frames may have an (assigned) number of tone units. Accordingly, if a feature is detected in such image or frame, the feature's tone may be utilized for all such tone units. The tone assignments may be as to features generally or specifically. For example, if two features have the same parameters as to the applied combination of velocities, etc., a general assignment scheme may assign the same tone to both features, while a specific assignment scheme assigns a first tone to one feature and a second, different tone to the other feature.

In certain embodiments, more than one feature may be detected in any given image or frame of a swing's imaging. For example, for a first theoretical frame, a body rotation movement may be detected along with a club movement. Accordingly, as to feedback associated with such image or frame, the feedback generator may assign a tone for each such detected swing parameter (e.g., one for the body movement and one for the club movement). As such, that associated feedback may be a combination of tones. Indeed, from frame to frame, combinations of detected features may change, such that the combination of tones may be varying.

As another example, feedback generation systems or methods may provide a tone as feedback to the user for a predetermined feedback period. That feedback period may be variously provided. As an example, the feedback period may correspond to the time period of the image or frame in which the feature was detected; in that case, the tone may be provided for the tone units associated with such image or frame. As another example, the feedback period may include not only the time period of such image or frame, but also some additional time period, e.g., a configured number of subsequent, adjacent tone units.

In accordance with various embodiments, during any feedback period (whether or not including such subsequent tone units), the tone may be subject to a tone envelope. A tone envelope may include an attack period, a decay period, a sustain period and a release period (an "ADSR envelope"). The tone envelope may also include a hold period: e.g., if any image or frame exists in which no feature is detected (a "null period"), one or more tones associated with the immediately prior image or frame (or the next prior image or frame having a feature) may be held as per the sustain period, so as to bridge the null period. A hold period may not be applicable to the initial image or frame.

In accordance with various embodiments, a combination of tones may be variously implemented. For example, each tone of a plurality of tones may simply be combined with others for the duration of a feature. In such combination, each such tone has a given amplitude during its respective duration, and the overall amplitude is the sum of such tones' amplitudes. As an alternative, the overall amplitude may be subject to a maximum, such that tones may be combined so that each tone equally contributes to such overall amplitude. As yet another alternative, tones may be combined with sonic adjustments that vary among the combined tones. As an example, sonic adjustment may be based on priorities or other weighting responsive, e.g., to the (assigned) value of the associated swing component, such value being, for example, related to results. To illustrate, the tone of highest priority may be unchanged, while a tone of lower priority may be combined: at a priority-based, reduced amplitude relative to the highest priority tone; or the after adjusting its harmonic content (with or without maintaining its fundamental); or after changes to its ADSR envelope; or after changes in one or more other sonic features.

In certain embodiments, if the sonic characteristics associated with one image or frame are different than those of the subsequent image of frame, the transition there between may be conditioned so that, from a user-perception point of view, the transition is softened, smoothed or otherwise adjusted so as to enhance sonic appeal.

In certain embodiments, for a time period after the image or frame associated with the final detected feature, the feedback generator may provide terminating feedback. Such terminating feedback may include the tone(s) of the last image or frame of a detected feature. As an example, such terminating feedback may be implemented via applying and/or extending a hold period (see, e.g., ADSR envelope, above). Such terminating feedback may continue through any final imaging of the swing (e.g., even if no feature is detected in any images or frames of such final imaging). Such terminating feedback may continue for a selected time after imaging of the swing.

The tones may be variously implemented and determined. Each tone may be implemented via a system-determined fundamental harmonic and harmonic content. Moreover, the universe of user-available tones may be implemented via sound synthesizer technologies, including sampling technologies. Such synthesizer technologies may be variously implemented. As an example, the mobile app described above may include such technologies, together with a GUI that enables the user to select/configure operation, such as, e.g., configuring features, selecting (or de-selecting) voices, setting amplitudes or changing ADSR and/or Hold Period parameters, sampling sounds, etc. These descriptions as to feedback generation and administration apply to any feedback discussed herein.

Further aspects relate to providing feedback to an athlete's based upon the effect their athletic activity has on another physical object, such as a sporting device. For example, feedback signals may be provided based upon the trajectory and/or attributes of a golf ball's flight after being contacted with the athlete's golf club. In another embodiment, a basketball player's shot may be used to provide feedback to the player. In one embodiment, the athlete's effect on an object may be determined (see, e.g., block 610). As one example, block 610 may utilize one or more systems described in relation to block 604 and/or 802 to process a plurality of images to identify image data of the first athlete contacting (directly or indirectly) the physical object. In further embodiments, image data of an object in motion, such as after being contacted, may be utilized. Motion data may be utilized even if the athlete is not within the image data. In yet further embodiments, non-image sensor data may be used to obtain motion data based upon an object placed in motion or otherwise contacted by the athlete. For example, in one embodiment, a baseball may comprise an accelerometer that may be used to determine speed, spin, acceleration, or other motion parameters of the ball after being thrown by a pitcher and/or struck by a batter. Data from the accelerometer may be utilized alone or in conjunction with image-based data. Likewise, sporting devices, such as the batter's bat may comprise at least one sensor. In this regard, collecting and/or analyzing of the data of block 401 may incorporate any and all systems and methods disclosed herein, including but not limited to those described in FIGS. 68. In certain embodiments, the data collected and/or analyzed as part of block 410 will be entirely distinct from the data collected that relates to the athlete performing a feature of an athletic movement (e.g., block 404). Yet those skilled in the art will appreciate that in certain embodiments, block 410 may be utilized to determine whether a feature or movement occurred and/or an attribute of a performed feature or movement. In this regard, certain embodiments may incorporate block 610 before or during implementation of block 608.

Upon determining the effect of the athlete upon the physical object, such via block 610, feedback signals may be transmitted to the athlete. In one embodiment, block 608 may be initiated (or modified) to provide feedback signals to the athlete. The feedback signals may be of the same format and type as feedback signals relating to the athlete's performance of a prior or concurrent feature or movement. For example, if audio signals were used to convey attributes of the athlete's performance, then audio signals may also be utilized to convey feedback of attributes from the data relating to feedback of the athlete's effect on the physical object (which may be unrelated to the performance of a feature). In one embodiment, an audible tone may be modulated based upon attributes of a golfer's swing and a second audible tone may be modulated based upon attributes of the ball upon being hit with the club. In one example, a "sliced" ball may result in a first modulated signal and a "hooked" ball may result in the transmission of a second modulated signal. In certain embodiments, impact forces, speed, acceleration, location relative to a surface (such as the ground) or other attributes may be used in determinations of what feedback signal is utilized (and/or how a feedback signal may be altered based upon one or more attributes).

Further aspects of this disclosure relate to calculating an athletic score based upon the captured image data and/or data derived from the image data. Example embodiments contemplate analyzing captured data, in any combination of image data, sensor data, or swing results data, so as to provide feed-forward, i.e., coaching. Such feed-forward may be provided via a GUI of a portable electronic device, e.g., the GUI of an app or any computer-executable instructions on a non-transitory computer-readable medium executing, for example, on a device, such as portable device 112, which may be a smartphone that provides the camera. E.g., feed-forward audio may be provided. Such feed-forward may be beneficial to muscle memory training. Also, with a swing or other constituent being captured via an image sensor, the feedback that is generated for the athlete can be stored for replay with the stored video. This stored video may then be played back later, including repeatedly (e.g., if the swing had particularly good swing results data), for the purpose of muscle memory development.

In one embodiment, a sport-specific algorithm may be utilized to determine sport-specific score for the athlete. In one embodiment, a reaction value derived, at least in part, from image data, and optionally another performance attribute, may be utilized in a sport-specific ranking algorithm to obtain a single athletic score for the athlete. The score may correlate attributes of the athlete's performance (such as through data collected at blocks 604, 804 and/or 806) with a result (such as data collected at block 610). For example, a golfer's swing data may be compared with attributes of the struck golf ball. For example, certain tempos of a swing may be scored based upon the athlete's effect on the golf ball. In certain embodiments, a score may be used to rank the athlete and a second athlete according to their respective athletic scores. In certain embodiments, a trainer, coach, or athlete may merely have to transmit image data (such as a video) of the athlete performing physical activity. A system may be configured to analyze the image data (such as by implementing one or more of the processes described herein) to provide an athletic score. In one embodiment, the image data may be parsed to identify predetermined physical activities represented within the image data. In further embodiments, systems and methods may utilize the performance attribute(s), rating(s), and/or the image data to provide a training prescription.

Physical activities implicate motor coordination. Motor coordination is the combination of body movements created with kinematic (such as spatial direction) and kinetic (force) parameters. Motor coordination is achieved by effecting, as to a participant's body and/or body parts, a sequence of initial positionings/orientations, initial movements, subsequent parts of the initial movements, and subsequent movements. Motor coordination is enhanced by effecting such sequence in a well-structured manner, e.g., characterized by proper timing of an among movements, efficient movements, and smooth transitions between and among movements. Motor coordination, while fundamental to physical activities generally, may have elevated value as to some constituents of any particular physical activity. As to such constituents, superior motor coordination may deliver superior performance not only as to such element, but also as to the physical activity overall. As examples, motor coordination may have elevated value as to swinging any athletic equipment, including, e.g., baseball bats, tennis racquets, hockey sticks, lacrosse sticks, and any of the variety of golf clubs. As further examples, motor coordination may have elevated value in launching any athletic equipment, including, e.g., pitching a baseball, throwing a football, shooting a basketball, kicking a soccer ball, spiking a volleyball, putting a shot, or throwing a javelin. As further examples, motor coordination may have elevated value in delivering, throwing or otherwise performing any of, e.g., a dive, a vault, a tumble, a dance spin, a roundhouse kick or a punch. It is understood that, herein, the terms "feedback test", "performance test" or "test", or variants thereof, may refer to anything relating to participant feedback (including, e.g., feedback as to motor coordination, whether generally or as to any one or more characteristics), such as, as examples, the acquisition of imaging (as set forth herein), the analysis of such imaging, and/or the generation/provision of such feedback) In example is understood that, herein: (i) the term "physical activity" contemplates any physical activity involving motor coordination, including, without limitation, any of sports and other activities referenced above or otherwise herein; (ii) the term "constituent" contemplates any portion, part, element or other constituent movement or movements of any such physical activity; and (iii) although any particular description herein may reference any one constituent or any one physical activity, such description is only for purposes of explication, simplicity or example, and not to limit the descriptions hereof to such constituent or activity, such that, for example, if the terms "swing" or "swinging" are used herein, those terms are used not only to describe all swinging-type constituents (regardless of the any equipment the user swing or swings from), but also all non-swinging movement/movements, including, without limitation, all of the foregoing non-swinging constituents.

In example embodiments, a constituent may contemplate component(s) and an activity space. An activity space manifests the physical context associated with a physical activity including one or more constituents thereof, such physical context generally comprising test elements. An activity space may be variously implemented, including, e.g., one or more test elements (such as, boundaries, area(s), equipment, and the like). A component may contemplate any of, e.g., participant's body position, an participant's body orientation, movement of one or more body parts, or other action involving the participant, or an absence or substantial absence of any of same; or a change as to any of same; or a change of state of a test element (e.g., equipment changing state, such as being swung, released and/or landing) as relates to the participant's performance of the activity or one or more constituents. A component contemplating an participant's body position or orientation may comprise, as to the participant's body or body parts, relative positioning or orientation among two or more body parts, or positioning or orientation of the body or body part(s) relative to one or more test elements, or combinations of same.

Figure 9A:
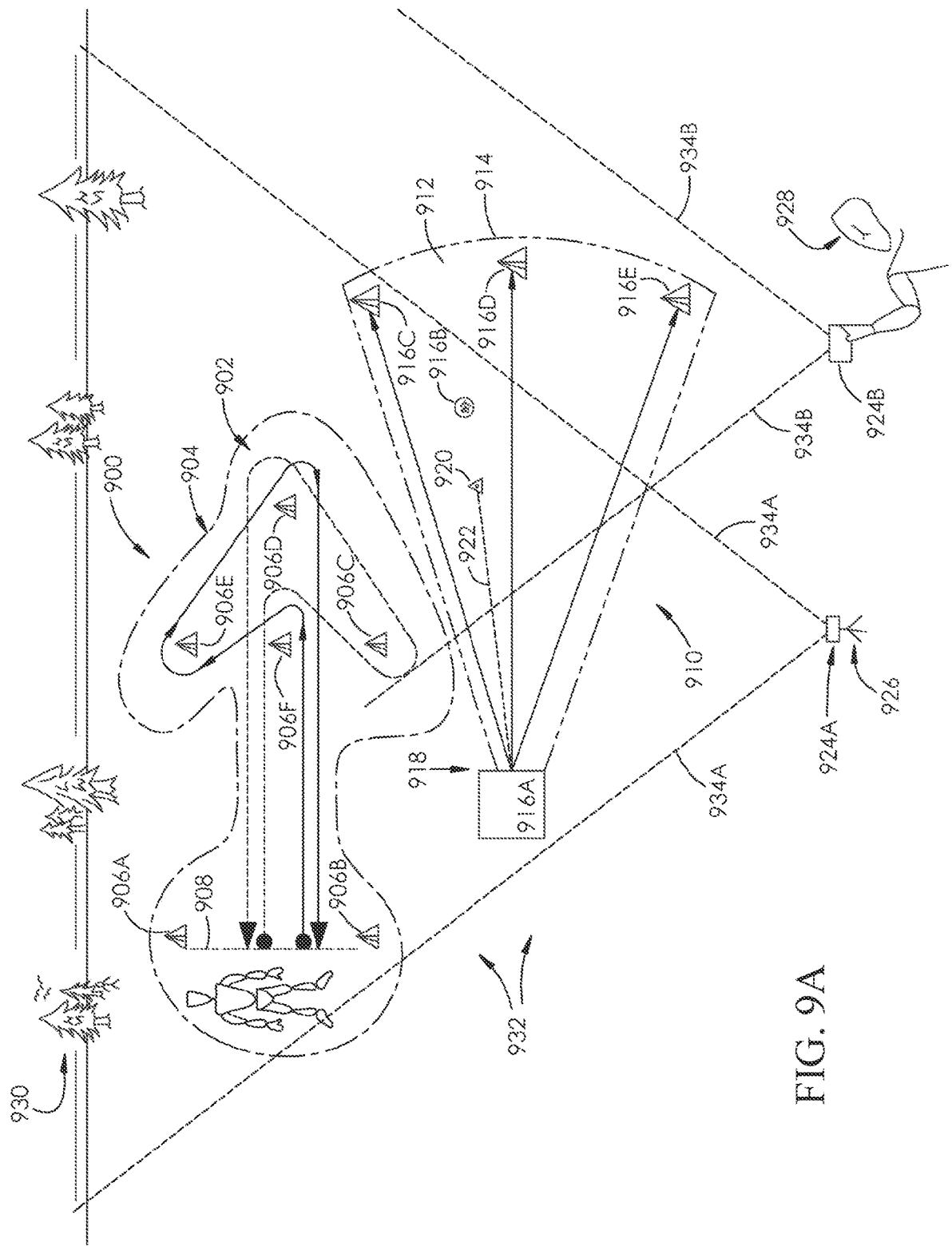
FIGS. 9A and 9B show an example activity space comprising illustrative test elements.
Figure 9B:
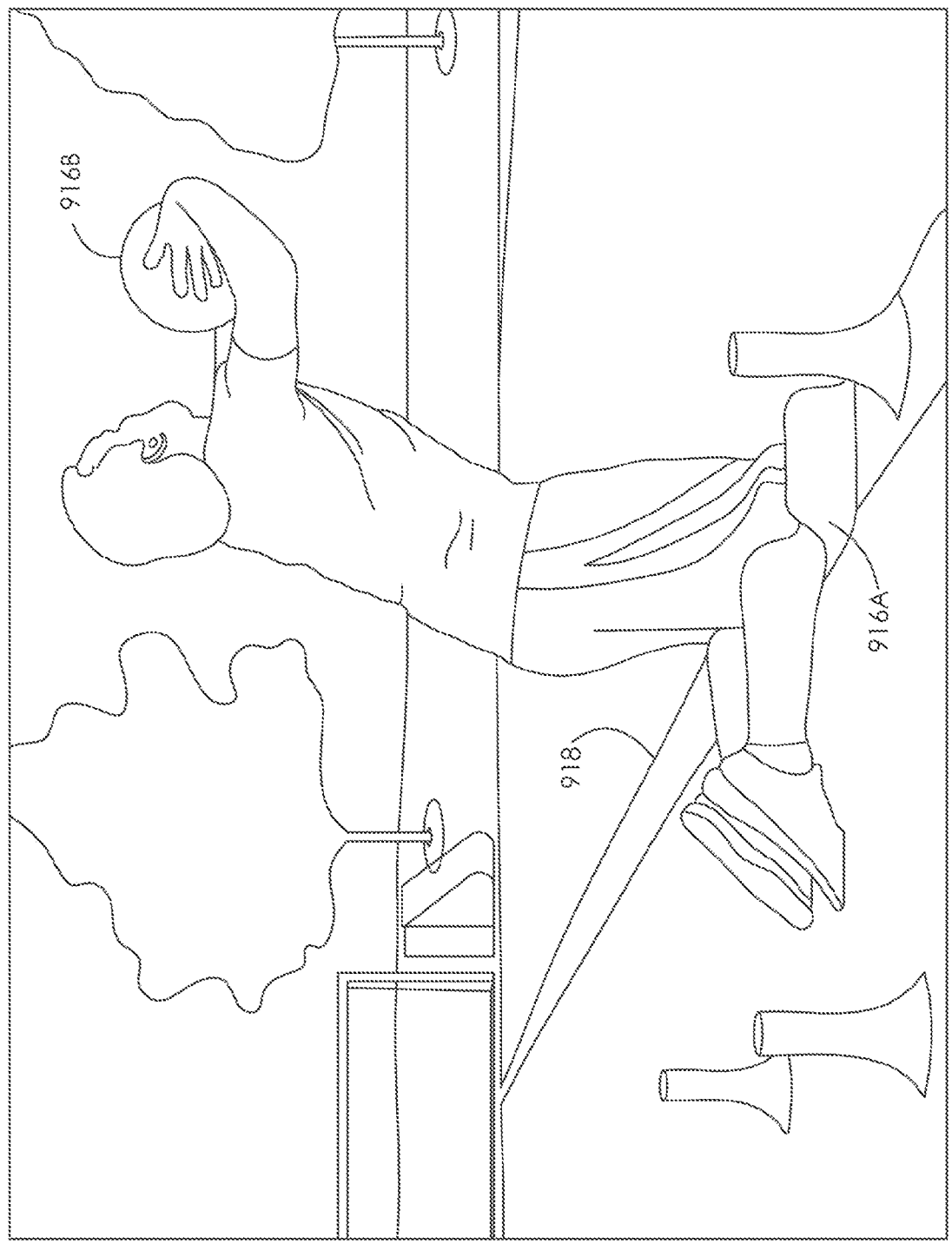

FIGS. 9A and 9B show example activity spaces comprising illustrative test elements. With reference to FIG. 9A, activity space 900 illustrates example test elements. Activity space 900 is associated with an Arrowhead Agility performance test, which test may be various configured with respect to test elements. As to test elements, activity space 900 may include area 902, equipment 906A-F, and a start-finish line 908 (referred to sometimes herein by the term "start-stop line"). The area 902 may have a boundary 904, which boundary may or may not be defined, demarcated or otherwise observable/known by the participant (herein after, the terms "participant", "athlete", "user" and the like may be employed and, unless a specific use states or implicates otherwise, the terms are used to refer to the person as to whom imaging of constituent(s) is being acquired for the purposes set forth herein). Within area 902, the equipment 906A-F may be positioned at prescribed locations, which equipment may thereby indicate to the athlete various locations for changes in direction or activities in performing the test. The equipment 906A-F may indicate to the athlete the start-stop line 908. In an example, the equipment 906A-F includes markers, such as cones, arranged in a predetermined formation: (i) four cones 906A, B, C, E are positioned to form a square with ten-meter sides; (ii) a cone 906F is centered on the line between cones 906C and 906E; and (iii) cone 906D is positioned on a line perpendicular to the line formed by cones 906C, 906F and 906E, at a distance, e.g., five meters, from 906F, distally from cones 906A, B. The area 902 may be established in, e.g., a portion of a yard, a field, a park, a sporting field, a parking lot, or any other area that adequately supports the athlete's proper performance of the performance test. In this example, area 902 is anticipated to be a level, firm, non-slippery surface, etc. or at least substantially so (e.g., absent ridges, raised obstacles, holes, bog, mud, slick areas, etc.). In example embodiments, activity space 900 may exclude any one or more of the foregoing, including all of the foregoing, or may include any one or more of the foregoing in combination with one or more alternative or additional test elements.

With further reference to FIG. 9A, the activity space 900 may include various test elements other than those described above. In example embodiments, test elements may include one or more of the following, e.g.: (i) the athlete starts on or behind the start-stop line 908 (e.g., all points of the stance are on or behind, but not over, the start-stop line 908); (ii) no cone may be touched or otherwise disturbed at any time; (iii) on the respective run from the start-stop line 908, cones 906F, 906E, and 906D are to be rounded, in that order, in the directions shown in FIG. 9A, with each cone not being stepped over; (iv) on the respective run from the start-stop line 908, cones 906F, 906D, and 906D are to be rounded, in that order, in the directions shown, with each cone not being stepped over; (v) on the respective runs from cone 906D toward the start-finish line 908, the run is between either cones 906F and 906E, or cones 906F and 906C, as shown in FIG. 9A; (vi) a predetermined number of repetitions are performed (e.g., four repetitions, with 2 in each direction); and/or (vii) between each repetition, a predetermined latency ('recovery interval') is employed (e.g., a max of 5 minutes between each repetition, with or without a minimum recovery period). In example embodiments, test elements may exclude any one or more of the foregoing, including all of the foregoing, or may include any one or more of the foregoing in combination with one or more alternative or additional test elements.

In various implementations, an activity may contemplate various constituents, and each constituent may contemplate various components performed in an activity space. In an example, wherein the activity is an Arrowhead Agility exercise, constituents or components may include one or more of the following, e.g.: (i) the athlete assumes a prescribed, initial position (e.g., four-point sprinter's stance, three-point football stance, two-point runner's stance); (ii) the athlete, in stance, remains motionlessness or substantially motionlessness (e.g., no rocking, forward lean or counter-movement) for a prescribed time prior to activity or constituent start (e.g., 1 or more seconds, or such other time, and in any case so as to support the purposes hereof and, in some examples described herein, in image processing); (iii) the athlete's first movement or substantial movement defines test start (e.g., movement of a particular body part, or movement of plural body parts, or relative movement among plural body parts, or aggregate body movement); (iv) the athlete's time from the start-stop line 908 to initiation of rounding of cone 906F; (v) while rounding cone 906F, relative positioning or orientation among two or more body parts, or positioning or orientation of the body or body part(s) relative to cone 906F and/or the ground, or combinations of same (e.g., seeking maxima or minima, or other statistical indicia respecting the component); (vi) athlete's time from cone 906F to cone 906E (e.g., the time from completing the rounding of cone 906F to initiation of rounding of cone 906E); (vii) while rounding cone 906E, relative positioning or orientation among two or more body parts, or positioning or orientation of the body or body part(s) relative to cone 906E and/or the ground, or combinations of same (e.g., seeking maxima or minima, or other statistical indicia respecting the component); (viii) athlete's time from cone 906E to cone 906D (e.g., the time from completing the rounding of cone 906E to initiation of rounding of cone 906D); (ix) while rounding cone 906D, relative positioning or orientation among two or more body parts, or positioning or orientation of the body or body part(s) relative to cone 906D and/or the ground, or combinations of same (e.g., prescribing maxima or minima, or other statistical indicia respecting the component); (x) athlete's time from cone 906D to start-stop line 908 (e.g., the time from completing the rounding of cone 906D to reaching start-stop line 908); and/or (xi) test completion being when the athlete has crossed the start-stop line 908 (e.g., such crossing may be when any body part, specific body part(s) or the entire body has intersected such line, or has wholly passed beyond such line in the direction distal from cone 906D. (As per the above, any intermediate or interposed point between test start and test completion may sometimes be referred to herein as "test milestone".) In example embodiments of an Arrowhead Agility exercise, constituent and/or components may exclude any one or more of the foregoing, including all of the foregoing, or may include any one or more of the foregoing in combination with one or more alternative or additional constituents/components.

As to the example Arrowhead Agility exercise, test results (as described below) may be assessed from the total elapsed time from test start (see above re: first movement associated with the athlete's initiation of the performance test) to test completion (see above re: crossing the start-stop line 908). Other test results may or may not be assessed from one or more of the other listed, or of alternative or additional, constituents and/or components, alone or in any combination.

Further referencing FIGS. 9A and 9B, activity space 910 illustrates other example test elements. Activity space 910 is associated with a kneeling power ball chest launch exercise, which exercise may be variously configured with respect to test elements. As to test elements, activity space 910 may include an area 912, equipment 916A-E, and a launch line 918. The equipment 916B may be a power ball (e.g., a fitness ball, such as a medicine ball, of prescribed weight). The equipment 916A may indicate to the athlete the launch line 918. Moreover, in example embodiments, the equipment 916A may include a pad, rug, or other surface, which may be planar or flex to the surface beneath, on which the athlete may kneel (e.g., comfortably) to perform the test, i.e. to launch the power ball 916B. The area 912 may have a boundary 914, which boundary is shown in the example embodiment of FIG. 9A as generally demarcated, but which boundary in other example embodiments may or may not be defined, demarcated or otherwise observable/known by the athlete. As shown, within the area 912, the boundary is generally demarcated by equipment 916A and 916C-E positioned at prescribed locations, whereby the equipment indicates the boundary 914 wherein the ball may be thrown in performing the test. The equipment 916C-E may include cones placed at prescribed distance(s) from the equipment 916A and/or launch line 918 (e.g., the distances may be one or more radial distances so that the equipment 916A, 916C and 916E describe an angle, which angle may be bisected by the line formed between equipment 916A and equipment 916D). The area 912 may be established in, e.g., a portion of a yard, a field, park, a sporting field, a parking lot, or any other area that adequately supports the athlete's proper performance of the performance test. In example embodiments, activity space 910 may exclude any one or more of the foregoing, including all of the foregoing, or may include any one or more of the foregoing in combination with one or more alternative or additional test elements.

With further reference to FIG. 9A, the activity space 910 may include various test elements other than those described above. In example embodiments, test elements may include one or more of the following, e.g.: (i) in an initial, kneeling position, the athlete's knees may be on, or behind, but not over the launch line 918; (ii) so kneeling, the athlete's knees are to be parallel, and the athlete's feet are to be plantar flexed, i.e., pointed away from the launch direction, with the toes flush to ground, pointed or substantially pointed (e.g., the toes may not be curled so as to provide additional bracing force to the ground); (iii) the ball is to be grasped with both hands, the hands being aligned with a diameter of the ball and being positioned on opposite sides of the ball; (iv) the knees are to remain in contact with the ground or kneepad until at least the release of the ball (e.g., the complete release of the ball, such that no portion of the ball remains in contact with any part of the athlete's body); (v) the ball 916B is to land within boundary 914; and (vii) the athlete's body or portions of the body may not cross the launch line until the ball is fully released. In example embodiments, test elements may exclude any one or more of the foregoing, including all of the foregoing, or may include any one or more of the foregoing in combination with one or more alternative or additional test elements.

With reference to FIGS. 9A and 9B, a kneeling power ball chest launch exercise may contemplate various constituents and/or components performed in activity space 910. For example, constituents or components may include one or more of the following, e.g.: (i) the athlete assumes a prescribed, initial position (e.g., kneeling, with the back erect and facing toward equipment 916C-E), while holding the arms (including the ball 916B) out and above the head); (ii) the athlete, in the initial, kneeling position, remains motionless or substantially motionless (e.g., no rocking or similar movement) for a prescribed time prior to test start (e.g., 1 or more seconds, or such other time, and in any case so as to support the purposes of motionlessness in athleticism rating and, in some examples described herein, in image processing); (iii) the athlete's first movement or substantial movement (e.g., the ball being brought down to the chest as the hips are brought back to the heels); (iv) the athlete's movement of a particular body part, or movement of plural body parts, or relative movement among plural body parts, or aggregate body movement, relating to the translating the ball forward and up toward the release point; (v) the athlete launches the ball via both hands, without favoring one arm, without a throwing rotation of either arm and without rotation about the spine; (vi) test start, i.e., the athlete's release of the ball; and, (vii) test completion, i.e., the ball landing, e.g., at a landing point 920 at a distance 922 from the launch line 918, in a direction toward equipment 916C-E. In example embodiments of a kneeling power ball chest launch exercise, constituents and/or components may exclude any one or more of the foregoing, including all of the foregoing, or may include any one or more of the foregoing in combination with one or more alternative or additional constituents/components.

As to the kneeling power ball chest launch exercise, test results (as described below) may be assessed, e.g., as the distance between the launch line 918 (e.g., the edge in the direction of the equipment 916C-E) and the landing point 920 (e.g., the central point of the where the ball first lands). Such test results may be obtained from the elapsed time between the release of the ball and the ball landing. Additionally or alternatively, such test results may be obtained by a computation following from the flight time from release to landing. Other test results may or may not be assessed from one or more of other listed, or alternative or additional, constituents and/or components, alone or in any combination.

Some test elements associated with activity spaces 900 and/or 910 are shown in FIG. 9A, while others are not. Additional test elements may include ambient conditions, such as, e.g., wind speed and direction, ground condition, rain or other precipitation, temperature, humidity, and the like. Violations of one or more of these conditions may or may not void the test. In example embodiments, the conditions may be employed to annotate the test results. As another example, the conditions may be factored into the performance test, including, e.g., to adjust the test results for comparison or to modify the scoring or rating employing non-adjusted test results.

In example embodiments, the athlete's performance of performance test(s) is measured and/or otherwise converted into representative data (herein, such measurement and/or conversion is sometimes referred to by the term "measurement", as well as its derivatives thereof; and, such representative data sometimes is referred to by the term "test results"). In example embodiments, measurements may include dimensional metrics, such as, e.g., time (e.g., elapsed time, of a run, jump or agility test, or of a thrown ball's flight), distance (e.g., distance of an object's flight), angle (e.g., angle of change in direction), and/or position (e.g., one body part relative to another or relative to a reference, such as the ground or an obstacle). In example embodiments, measurements may include non-dimensional metrics, such as, e.g., counts. Such non-dimensional metrics may be applied to, e.g.: (i) repetitions, e.g., a count of executions of constituent(s) and/or component(s) in a performance test (for example, total number of push-ups executed in a fixed time, whether the execution is proper or not); and/or (ii) fouls, e.g., a count of errors in a performance test (for example, total number of push-ups in which the athlete bounced their chest off the ground).

Fouls and any associated foul metrics may be implemented variously within a performance test. Implemented "fouls" may be associated, e.g., with the athlete's improper execution of one or more components or constituents and/or with the athlete's improper departure from an activity space. An athlete's improper execution of a component or constituent may include, as examples: crossing of legs/feet during a shuffle movement (e.g., wherein a proper shuffle contemplates movement via legs/feet repeatedly being separated and then brought together, without crossing); failing to reach or exceed a threshold angle among body parts (e.g., a knee bend in a lunge or a squat); and/or tumbling or other gross loss of body control. An athlete's improper departure from an activity space may include, as examples: moving or being outside any area or boundary inside which a performance test is to be performed (e.g., in the kneeling launch test, throwing the ball outside the boundary 914); disturbing a test element (e.g., upending a cone in an agility course); failing to interact properly with a test element (e.g., failing to touch a cone when such touch is a test element; or touching a cone when not touching is a test element; or failing to round a cone or to stay to the inside or outside of a cone; etc.); failing to abide a test element (e.g., failing to maintain prescribed time conditions, such as motionlessness for a set time, or executing a repetition after a latency period and/or recovery interval has expired); and/or improperly exploiting a test element (e.g., pushing or pulling on a course marker as impetus for a test's change-of-direction, or bouncing one's chest off the ground as impetus for the upward movement in a push-up).

In example embodiments, foul(s) and any associated metric(s) may be consequential. Consequences may be variously implemented, including, e.g.: (a) disqualification (aka rejection) of a test result (such as responsive to, e.g., any of: a false start, a running start, an improper ball grasp during or rocking movement in a kneeling power ball chest launch test, assuming a position that delivers an unfair advantage in a test; a foul exceeding a predetermined threshold; any/or an aggregate foul count exceeding a predetermined threshold); (b) adding a predetermined time quantum to a test result measured via of time metric, e.g., such time quantum being responsive to the time benefit accrued due to the improper movement, possibly together with a penalty (e.g., 0.02 seconds for each upended cone, wherein the benefit to the athlete's time is predetermined to be 0.01 seconds for each such upended cone and wherein 0.01 seconds is assessed as a penalty); or (c) subtracting a predetermined distance quantum to a test result measured via of distance metric, e.g., such distance quantum being responsive to the benefit accrued due to the improper movement, possibly together with a penalty. In example embodiments, the resultant test results are the test results from measurement, as subjected to any adjustment (e.g., via disqualification, addition, subtraction or otherwise).

In example embodiments, only consequential fouls are detected, measured and acted on, such as being reported as to, treated or otherwise included in or with, test results. In example embodiments, consequential fouls may be acted on by negating test results. In example embodiments, non-consequential fouls may be detected (alone or together with consequential fouls), which detection may be acted on, e.g., for coaching or other direction, such as to instruct the athlete toward addressing such fouls and, thereby, enabling improvement of test results.

In example embodiments, the athlete may be enabled to obtain image data toward proving participant feedback as described herein, e.g., via use of one or more portable electronic device(s) 924A, 924B, which device(s) support capabilities further described herein, which capabilities include, but are not limited to, image acquisition capabilities, particularly acquisition of a sequence of images (e.g., such sequence of images including video frames and/or still images) with acquisition parameters so as to enable sufficient image data for image processing to yield outputs that, in turn, enable provision of, e.g., participant feedback. In example embodiments, such portable electronic device(s) may include a general purpose device, such as a smart phone (e.g., the HTC One X+) or may be a special purpose device (e.g., integrating capabilities specifically to provide a system and/or method in accordance with the descriptions herein). In example embodiments, each such device's image acquisition capabilities are used to acquire images of an activity, including as to one or more constituents, as well as components thereof. As shown in FIG. 9A, a portable electronic device 924A/B may be arranged by or for the athlete in association with the respective activity space 900, 910. So arranged, the portable electronic device 924A/B may be enabled to acquire images of the athlete's conduct as to the activity.

A device 924 may be arranged to enable such image acquisition in various manners, including, e.g., by a mount or by being hand held. As shown in FIG. 9A, the athlete may arrange a portable electronic device 924B so that it is held by a second person (e.g., a friend, teammate or another athlete also self-directing their own performance tests, etc.). As also shown in FIG. 9A, the athlete may arrange a portable device 924A via a mount on a tripod 926, whereby the mount enables the device's field of view 934A for image acquisition to be directed so as to cover the respective performance test. Alternatively, and provided such image acquisition is enabled, the athlete may otherwise arrange a device 924 via other mounts or other fixed devices (herein referred to collectively by the term "mount" and its derivatives), including via, e.g.: (i) placement directly on turf or ground (e.g., if the activity space is an outdoor field, such as a playing field); (ii) placement directly on a court (e.g., if the activity space is a basketball, volleyball or other indoor court); (iii) insertion in a bag pocket; or (iv) mounting on an item located in association with the activity space (e.g., a tree, a basketball post, a football post, a lamp post, a wall, etc.). Alternatively, another individual 928, which may be a trainer, coach, friend, colleague or other person, may hold and/or operate the portable device 924.

Among these arrangements, a device 924 may be provided with lesser or greater stability. When arranged via a tripod 926, a device 924 typically is provided with substantial stability. When arranged via a mount other than a tripod 926, a device 924 typically is yet provided with a level of enhanced stability, at least as compared to a hand-held arrangement. By contrast, when in a hand-held arrangement, a device 924 may be provided with less stability, or inconsistent stability, as compared to a mounted arrangement.

When stably arranged, e.g., via a tripod 926, a device 924 tends not to move, or not to move substantially, during image acquisition of a performance test. That stable arrangement typically enables image acquisition without, or with insubstantial, impact as to the acquired images and associated image data. A less stable arrangement—or an arrangement providing stability below a minimum threshold (e.g., under ambient conditions)—tends to subject acquired images and associated image data to a non-insubstantial impact. Such impact may include, e.g., aberrant motion of objects in the imaging. As an example, the device's physical movement may cause an object to appear to have motion among the images, notwithstanding that the object's corresponding physical item may have been stationary during the images' acquisition. As another example, if an object's corresponding physical item were to have actually been moving during the images' acquisition, the object may appear to have motion that is greater or lesser than the corresponding item's actual, physical movement. With aberrant motion of objects caused by the device's physical movement (e.g., physical movement of the device's imaging acquisitions capabilities, particularly the imaging chip), all objects of the images are impacted. Accordingly, in example embodiments, systems and methods contemplate employ of image processing technologies for detecting, estimating and otherwise addressing such aberrant motion, which technologies may be selected not only for capabilities re such addressing role, but also for compatibility with the image-based measurements as to performance tests as contemplated herein and, thus, to support provision of participant feedback.

As previously described with reference to FIG. 9A, a portable electronic device 924A, 924B may be arranged so that the device may be enabled to acquire images as to a performance test. In example embodiments, in acquiring images, a portable electronic device is not only arranged to enable image acquisition generally, but also positioned to provide proper image acquisition (i.e., image acquisition enabling image processing technologies to yield outputs enabling image-based measurements as to performance tests). Such positioning may respond to various factors, including, e.g., (i) the applicable test's activity space (e.g., physical dimensions) and (ii) the focal length, aperture and quality of the device's imaging lens, as well as the format/resolution applicable to the imaging. Generally, the lens' focal length is indicative of (i.e., inversely proportional to) the device's field of view 934A, B, while the focal length/aperture are indicative of the depth of field. The imaging's format/resolution is indicative of the amount of image data.

As an example with reference to FIG. 9A, a portable electronic device 924A may be positioned so that the device's field of view 934A enables image acquisition of the athlete as the athlete conducts the Arrowhead Agility exercise. In such positioning, the field of view 934A covers the entirety of the activity space 900, so as to enable imaging of all of the athlete's activities throughout the test. However, in order to cover that entirety within the field of view 934A, the device 924 may be positioned at a distance from the activity space 900 which distance has the activity space 900 toward, or even effectively in, the imaging's background 930. As well, the device 924 may be positioned at a distance which has the activity space 900 partly in the imaging's background 930 and partly in the imaging's foreground 932. In either case, one or more objects (such as, the object that corresponds to the athlete) may be insufficiently imaged, such that insufficient image data is available for image processing technologies to yield outputs enabling image-based measurements as to constituents and/or components and, thus, to support provision of participant feedback. In example embodiments, systems and methods contemplate employ of image processing technologies for detecting improper positioning, including, e.g., to notify the athlete to re-position.

As shown in FIG. 9A, a portable electronic device 924A, 924B may be properly positioned whether or not the field of view 934A, 934B covers the entirety of the performance test. As an example, as shown in FIG. 9A, the device 924A may be properly positioned and have its field of view 934A covering the entirety of the activity space 900 as to the arrowhead agility performance test. However, the device 924A, so positioned, has its field of view 934A not covering the entirety of the activity space 910 shown in FIG. 9A, which space 910 is associated with the kneeling power ball chest launch performance test. As to at least the portion of the activity space 910 that is not covered by the field of view 934A, a second portable electronic device 924B, via its field of view 934B, may be employed in order to provide entire coverage of the kneeling power ball chest launch performance test. Accordingly, in example embodiments, systems and methods may contemplate employment of communication/control technologies and/or image processing technologies, so as to variously coordinate plural portable electronic devices 924 (e.g., calibration, shutter synchronization and/or offsets) and process among such devices' plural sequences of acquired images (e.g., mosaic processing).

In example embodiments, a portable electronic device 924A, 924B includes image acquisition capabilities. In example embodiments, a portable electronic device 924A, 924B includes not only image acquisition capabilities, but also other capabilities, including, e.g., one or more of: (i) processing capabilities; (ii) communication capabilities (e.g., supporting wireless communications for communications/control among portable electronic devices 924, as well as with other sensor, electronic or computer devices); (iii) networking capabilities (e.g., for communications in any one or more networks, such as body area networks (BAN), personal area networks (PAN), local area networks (LAN) and wide area networks (WAN)); (iv) data acquisition capabilities (e.g., via one or more sensors internal or external to the device 924, such as one or more accelerometer(s), gyroscope(s), compass(es), other magnetometers, barometer(s), other pressure sensor(s), thermometer(s), other temperature sensor(s), microphone(s), other sonic sensor(s) (e.g., ultra-sonic sensor(s)), infrared (iR) sensor(s), and/or other electromagnetic radiation sensor(s)); (v) input/control capabilities (e.g., including via physical buttons, logical buttons enabled via a touch screen, voice input controls, and/or other input controls); (vi) output/notification capabilities (e.g., via LED light(s), a display, a touch-sensitive display, speaker(s), other audio transducer); and/or (vii) location detection capabilities (e.g., for identifying location(s) relative to other devices 924, or relative to sensors, equipment, or devices, or relative to test elements or the activity space, such as by GPS, AGPS signal analysis, signal strength measurements, or other technologies, including via data acquired from sensors, transceivers or other electronic devices embedded in equipment, apparel, footwear and/or accessories, and/or in other device(s) 924, including in combination(s), and/or in combination(s) with other devices 924).

In example embodiments that include processing capabilities, such processing capabilities may be implemented so as to execute, or cause to be executed, one or more sets of software instructions, including, e.g., mobile software application(s) and/or embedded applications, and/or operating system(s). Such processing capabilities, executing one or more such software instruction set(s) may be implemented to control such image acquisition capabilities, in whole or in part (such software instruction set(s) herein sometimes referred to by the term "image acquisition software"). Such processing capabilities and image acquisition software, either alone or together, may enable, one or more of, as examples: acquisition of one or more sequences of images (e.g., sequences of still images and/or video frames, which sequences of images and/or frames are herein sometimes referred to by the term "images" or "imaging"); control of the start and stop of each such sequence (including, e.g., coordinating among plural devices' imaging acquisition capabilities); control of any latency applicable to any sequence (e.g., delay between sequences and/or time offset for starting acquisition, such as against a reference or among plural devices' image acquisition capabilities); control of the acquisition frequency (e.g., frames or images acquired per unit time); control of the resolution and/or formatting applicable to the imaging (e.g., total pixels per image or frame, and/or the number of lines per image or frame and the number of pixels per line); control of any pre-processing of acquired image data (e.g., imager noise reduction, contrast control, etc.); and/or, control or selection of other imaging parameters.

In embodiments that include processing capabilities, such processing capabilities may be implemented so as to execute, or cause to be executed, one or more sets of computer-executable instructions on one or more non-transitory computer-readable mediums implementing one or more image processing technologies (such example instruction set(s) herein sometimes referred to by the term "image processing software"). In example embodiments, such image processing software includes image processing technologies directed to processing, analyzing, and otherwise extracting information from the one or more sequences of images acquired with respect to one or more constituents and/or components. In example embodiments, such image processing software may implement one or more technologies, including, e.g., any of various technologies of or relating to computer vision. In example embodiments, such image processing software may implement one or more image processing technologies sometimes referenced, sometimes among other terms, as: sequential frame analysis; sequential image analysis; image sequence analysis; video sequence analysis; stixel motion analysis, optical flow analysis; motion vector analysis; frame motion analysis; motion estimation; feature-based motion estimation; motion detection; change detection; frame differencing; sequential image differencing; segmentation; feature (based) segmentation; object segmentation; color segmentation; intensity segmentation; motion (based) segmentation; change detection segmentation; feature extraction; object recognition; pattern recognition; pattern matching; position estimation; background subtraction; image filtering; and global motion detection/removal (e.g., toward negating ego-motion). It is understood that the foregoing technologies list is not exhaustive. It is understood that the foregoing technologies list may include one or more generic among respective species, and/or components of either. It is understood that the foregoing technologies list may include one or more terms for the same, or substantially the same, or overlapping, technologies. It is understood that, in any employed image processing software, output(s) of any first of such listed technologies may be input(s) for such first or one or more second listed technology and, in turn, output(s) from such second listed technology or technologies may be input(s) for such second listed technologies or such first listed technology, in one or more iterations/recursions/updates. It is also understood that such software, supporting such technologies, may be configured to employ a priori knowledge of the performance test (e.g., test elements (e.g., the type of golf club), constituents, components, athlete height and/or other athlete characteristics, anticipated test duration(s), etc.) so as to enhance both acquisition of imaging sequences (e.g., via sufficiently early start, and sufficiently late termination, of acquisition relative to the conduct of the activity, constituent and/or component) and analysis of imaging as described herein (e.g., to advance segmentation/detection/motion estimation among objects, including in phases among objects and sub-objects, such as, in a first phase, analysis as to general movement, such as of the athlete's body and, in a second phase, analysis of specific or relative movement of/among the athlete's body, head, torso, arms, legs, equipment etc.). It is also understood that any image processing technologies generally provides for processing of (i) still images (individually or as some set or sequence), (ii) video or videos (e.g., plural video clips, such clips having a known relationship there among in re a performance test); and/or (iii) any combination of still image(s), video, and/or videos. (Any such processing, such as via any such image processing technologies, may sometimes be referred to herein by the term "image processing".)

In example embodiments, such processing capabilities executing image processing software may be implemented so as to process, or cause to be processed (e.g., via the device's one or more operating system(s) or embedded software instruction sets), one or more sequences of images acquired with respect to one or more performance tests toward yielding outputs for enabling provision of participant feedback, e.g., for one or more constituents and/or components. In various example embodiments, processing capabilities executing image processing software may be implemented so as to process, or cause to be processed (e.g., via the device's one or more operating system(s) or embedded software instruction sets), one or more sequences of images acquired with respect to one or more constituents and/or components, wherein such processing may be directed to one or more of the following operations, e.g.: (i) identifying images associated with the athlete's selected constituent(s) and/or component(s) described herein; (ii) detecting, confirming and/or monitoring test elements, via imaging (e.g., confirming arrangement of cones at proper locations and separations; confirming proper area properties, such as levelness and absence of obstacles, ambient conditions, etc.); (iii) identifying, detecting, confirming and/or monitoring components, via imaging (e.g., confirming the athlete assumes a prescribed, initial position and, in the initial position, the athlete remains motionlessness or substantially motionlessness for a prescribed time prior to test start; confirming athlete form, such as via relative positioning or orientation among two or more body parts before, at test start, or during conduct of, a test; confirming relative positioning or orientation of the athlete's body or specified body part(s) relative to a test element before, at test start, or during conduct of, a test); (iv) detecting, measuring and acting on fouls (e.g., detecting consequential and/or non-consequential fouls), as described herein; (v) detecting, estimating and otherwise addressing aberrant motion of imaging objects (e.g., aberrant motion caused by physical movement of the portable electronic device's image acquisition capabilities); and/or (v) detecting improper positioning of the portable electronic device 924A, 924B in the employ of its image acquisition capabilities respecting a constituent or component. It is understood that, in some example embodiments, processing capabilities executing image processing software may be implemented so as to exclude any one or more of the foregoing operations, including all of the foregoing operations, or may include any one or more of the foregoing operations in combination with one or more alternative or additional operations.

In embodiments that include processing capabilities, such processing capabilities may be implemented so as to execute, or cause to be executed, one or more sets of computer-executable instructions on one or more non-transitory computer-readable mediums implementing one or more feedback processing technologies (such instruction set(s) herein sometimes referred to by the term "feedback processing software"). Such processing capabilities, executing such feedback processing software, may be implemented to provide, from the outputs of the image processing software, either/both test results for one or more such performance tests and/or feedback as to one or more constituents and/or components, as described herein. In example embodiments, based on the image processing software detecting images associated, respectively with test start and test completion in the conduct of a performance test, the feedback processing software may be implemented to identify the number of images from the test start to the test completion and, based on the acquisition frequency, calculate test results for such conduct as an elapsed time. In example embodiments, based on the image processing software detecting images associated, respectively with test milestones arising in the conduct of a performance test, the feedback processing software may be implemented to identify the number of images from the test start to one or more selected test milestones, from any selected test milestone to any other selected test milestones, and/or from any one or more selected test milestones to the test completion; and, based on the acquisition frequency, calculate test results for such conduct as an elapsed time. In example embodiments, based on the image processing software detecting images associated, respectively with test milestones arising in the conduct of a performance test, the feedback processing software may be implemented to process images associated with any test milestone, or among selected test milestones, or among any selected test milestone and test start and/or test completion, such image processing being directed, e.g., to identify issues of form, or to identify opportunities to improve performance, or to otherwise enhance performance, such as for coaching, whether for self-coaching or for assistance from a coach, trainer or otherwise. In example embodiments, based on the image processing software detecting images associated, respectively a constituent (including one or more of its components) in the conduct of a performance test, the feedback processing software may be implemented to process such images, e.g., toward providing participant feedback, or toward identifying issues of form, or to identify opportunities to improve performance, or to enhance performance via coaching, whether for self-coaching or for assistance from a coach, trainer or otherwise. Such image processing and analysis as to form, e.g., may be directed to identifying, confirming, assessing or otherwise analyzing, as to the athlete's body or body parts, relative positioning or orientation among two or more body parts, or positioning or orientation of the body or body part(s) relative to one or more test elements, e.g., in or among test milestones, test start and/or test completion.

It is understood that, in one or more of the example embodiments described herein that employ a portable electronic device 924, such example embodiments may be implemented to employ, additionally or alternatively, device(s) other than a portable electronic device 924. It is also understood that, as to one or more of the example embodiments described herein, a portable device 924 may be implemented via general purpose architecture (i.e., hardware, software, etc. toward supporting operations different from, in additional to, or potentially in the absence of the imaging-directed operations described herein), or via an application specific architecture (i.e., hardware, software, etc. toward supporting only the operations described herein), or via another approach so that the device enables the operations described herein by means of some combination with one or more other devices. It is also understood that, as to one or more of the example embodiments describing processing herein, such processing may be variously executed, including, as examples: (i) via a portable electronic device 924 (e.g., via such device's internal processing capabilities); (ii) among portable electronic devices 924 (e.g., via communications and/or networking capabilities); (iii) among one or more portable electronic devices 924 in combination with one or more processing capabilities external to any such device 924; (iv) via processing capabilities external to any such device 924 (e.g., processing capabilities provided in association with one or more sensors, or by means of an athlete's device other than device 924, or through one or more remote processing center(s), or via cloud services), any one or more of which may be accessed via, a.o., an athlete's BAN, PAN, LAN or WAN; or (iv) at any time and over time, by any one of these, or among any combination of these (e.g., as arbitrated respecting and otherwise responsive to, a.o., processing volume, time constraints, competing processing constraints/priorities, power/energy demands/capacities, processing power, etc.).

Figure 10:
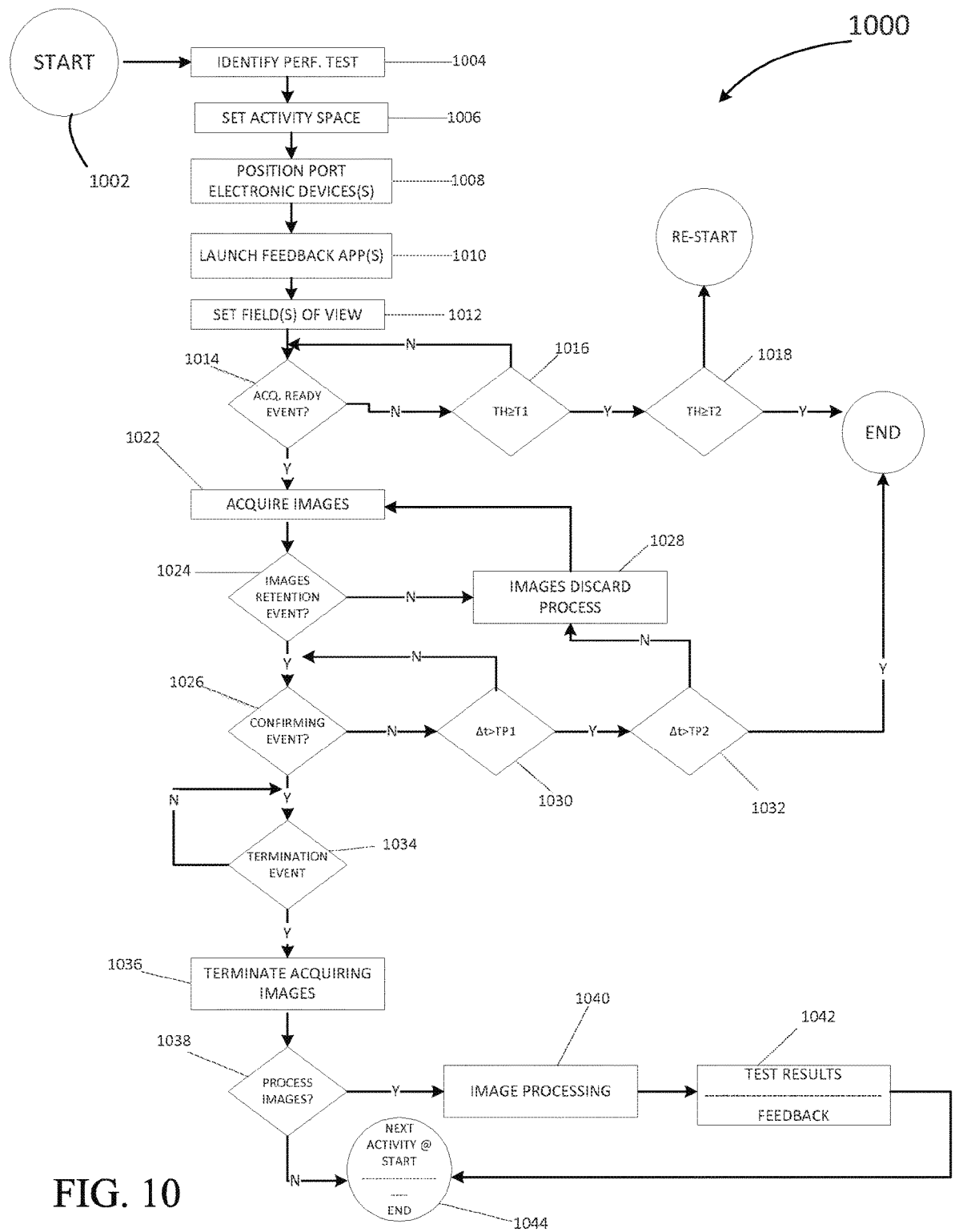
FIG. 10 is a flowchart of an example method that may be implemented to generate an athleticism rating using imaging data in accordance with certain embodiments.

Referring to FIG. 10, an exemplary method 1000 is illustrated for generating an feedback and/or test results, via imaging. At step 1002, labeled "Start", the method may be initiated. As an example, the method may be initiated by, e.g., an athlete electing to conduct a performance test. As another example, the method may be initiated iteratively, including, as examples: (i) if the athlete elects to conduct, in series, a battery of performance tests; (ii) as to any performance test, plural iterations of the test are prescribed; (iii) from images acquired during conduct of any performance test, image processing detects a foul, or other circumstances that negates the test and motivates starting anew; and/or (iv) an improper condition is detected (e.g., a tail wind when a sprinting performance test is anticipated), so as to motivate starting anew. In example embodiments, the athlete may so elect with or without employing any device 924 or otherwise. That is, the athlete may so elect by committing to conduct performance tests.

At step 1004, a performance test may be identified. In example embodiments, the athlete may identify a performance test without aid of any device. In other example embodiments, the athlete may employ a portable electronic device 924 (e.g., having a display and executing computer-executable instructions on a non-transitory computer-readable medium (e.g. mobile software application(s)), whereby the identification may be via a graphic user interface. Such graphic user interface may employ any of various user interface facilities (e.g., menus) to support identification, including, as examples, displaying supported tests so as to enable the athlete to select there among, displaying tests (by sport, activity, constituent and/or component), displaying tests as batteries (by sport, activity, constituent and/or component), displaying the current test in a series of tests so as to guide the athlete (e.g., through a battery of tests), displaying the tests that the athlete has previously conducted or indicated interest in conducting, and the like. In example embodiments, in this step 1004, the athlete may reject, select or confirm an activity, constituent and/or component.

At step 1006, the activity space may be set. In example embodiments, the athlete (alone or with assistance) may physically establish, deploy, obtain or otherwise set up the activity space, including as to any one or more of the test's area, boundary, equipment or other prescribed test elements. In example embodiments, the athlete may be enabled to do so via use of plural device(s) 924, or via use of the device(s) 924 in combination with, or via employ of, associated mechanisms, which mechanisms may or may not be electronic in nature. Electronic mechanisms may include or support ranging and orientation capabilities, including via compass, signal strength, laser ranging, or other facilities. Non-electronic mechanisms may include or support ranging and orientation capabilities via having defined size or markings. As to use of electronic mechanisms and/or plural devices 924, the devices 924 and electronic mechanisms may coordinate to determine distances via signal strength metering or other ranging there between, and orientation via, e.g., compassing. As to use of the non-electronic mechanisms, the devices 924 may determine distances and orientations by imaging, i.e., the ratio of imaged to actual size of the non-electronic mechanism(s) at candidate location(s), such locations oriented via, e.g., the device's compass.

At step 1008, portable electronic device(s) 1024 are arranged/positioned for image acquisition. As described herein, such device(s) may be arranged via various mounts or by being hand-held (e.g., by a person selected by the athlete). In this step, such device(s) may be positioned in association with the area/boundary of the activity space. Such positioning may be preliminary, in that the positioning may be adjusted to improve imaging acquisition (e.g., toward positioning the activity space in the imaging foreground 1032, as described herein, including with respect to step 1012 below).

At step 1010, as to example embodiments employing a portable electronic device 1024 that executes, or causes to be executed, one or more sets of software instructions, one or more of such instruction set(s) may be launched. In example embodiments, such instructions set(s) are directed to supporting participant feedback(s), as described herein. In example embodiments, at step 1010, launch may be directed to one or more of image acquisition software, image processing software, and/or feedback processing software, alone or in combination, including, in combination with one or more of, e.g., other mobile software application(s), and/or embedded applications, and/or operating system(s). In example embodiments, such image acquisition software, image processing software, and/or feedback processing software may be integrated (e.g., as an feedback processing "app").

At step 1010, as to example embodiments employing a portable electronic device 1024, such launch may be variously provided. In an example embodiment wherein the device 1024 is implemented via general purpose architecture (e.g., as a smart phone), launch may be provided, e.g., via an athlete (or assistant) touching an icon on a touch screen display, which icon represents the applicable software. In an example embodiment wherein the device 1024 is implemented via an application specific architecture, launch may be provided, e.g., when an athlete (or assistant) powers on the device. In either case, launch via step 1010 may be omitted if, at step 1004, the athlete identified the test via the device 1024, as described therein.

At step 1012, the field of view is set for image acquisition as to the activity space. In example embodiments wherein image acquisition capabilities are provided via portable electronic device(s) 1024, the athlete may arrange/position portable device(s) 1024 whereby the field of view 1034 is directed to cover some or all of the activity space associated with a respective performance test, as described herein.

In so arranging/positioning device(s) 1024 as to field of view, however, device 1024 may be arranged/positioned at a distance from the activity space 1000 which distance is sufficiently large as to risk one or more imaged objects (e.g., the imaging sequence's object that corresponds to the athlete) being insufficiently imaged for proper image processing. Other positioning, arrangement or other physical staging issues may also arise, including, as examples: (i) positioning that introduces lighting issues (e.g., sun or other bright light, or shadows or other low light, or other lighting that may impede proper image acquisition); (ii) positioning sufficiently proximate to or in the activity space so as to risk one or more imaged objects not being acquired at all or not fully acquired (e.g., although detection of the athlete's kneeling is sought, proximate positioning may cause imaging to omit objects corresponding to the athlete's knees); (iii) arrangement(s) in which camera movement is substantial, or excessively high (e.g., as to a hand-held imaging device, image motions sourced from device movement may be substantially or overly difficult to remove or otherwise address); and/or (iv) circumstances implicating excessive or overly confusing motion present in the sequence of images (e.g., besides the athlete, other active persons are in the field of view, particularly in the foreground of the activity space, in sufficient number and/or at sufficient activity level(s) as to impede image processing or confidence therein).

Responsive to issues arising from positioning, arrangement or otherwise relating to physically staging the device with respect to image acquisition, example embodiments, at step 1012, may implement pre-test image processing, i.e., toward one or more of: detecting any imaging issues; characterizing the issues; notifying the athlete of the issues; suggesting potential solutions or other means to address the issues; suspending or terminating next steps in operations, including until some or all issue(s) are resolved or sufficiently resolved; iterating any one or more of these; and/or shutting down. As described herein, in example embodiments, the device 924 may suggest re-positioning of the device.

In example embodiments, at step 1012 or other pre-test step, ambient conditions may be detected, analyzed (e.g., against test elements) and acted upon, as described herein. Such ambient conditions may be detected via device(s) 924, including via, e.g., (i) sensors, whether such sensors are internal to device(s) 924 or are external thereto, such as integrated into the athletes apparel, footwear or accessories or provided in other devices within the athlete's instant BAN, PAN, or LAN; (ii) data sources, which data sources may be accessible to the device(s) 924 based on LAN or WAN (e.g., where device(s) 924 comprise a smart phone, weather service entities may provide current local conditions via cellular or Wi-Fi connectivity, or other software may include feature(s)/function(s) enabling such data to be obtained. In example embodiments, ambient conditions may be analyzed and acted upon by, a.o. possibilities, precluding or voiding a test, or informing a change in the setup of the activity space (e.g., re-positioning the test elements so that a sprint is run with wind directed perpendicular to the running lane).

At decision 1014, example embodiments may implement an "acquisition ready" event test. In such step 1014, if an acquisition ready event is or has been detected, image acquisition will proceed. If such ready event is not or has not been detected, image acquisition will not proceed. In the latter case, example embodiments may provide for the test to be repeated until a ready event is detected. Other example embodiments may provide for the test to repeated until one or more configured threshold(s) are met or exceeded, e.g., number of repetitions, a timer expires (e.g., starting from launch or other reference), or otherwise. Such other example embodiments may provide for (i) repetition(s) of any of the foregoing steps, or components of the foregoing steps (e.g., identification of a performance test, or confirmation of a previously identified performance test, or pre-test image processing, or ambient conditions detection), or (ii) ending operations, or (iii) having repetitions subject to a first threshold (T1 at decision 1016) and re-starting or ending operations subject to a second such threshold (T2 at decision1018). A re-start may include, as examples, notification to the athlete via a device's output/notification capabilities (e.g., a visible warning signal, such as via a LED light; a warning screen splashed on the display; an audible warning signal sounded by speaker(s), or a combination of these). Alternatively, the process may terminate if the threshold is larger than T2 at decision 1018.

In example embodiments, an "acquisition ready" event may be variously implemented. As examples, a ready event may be implemented to be, as examples: (i) properly concluding any of the steps 1004-1012, or components thereof; (ii) properly re-positioning so as to enable image processing; (iii) engaging prescribed input/control capabilities of device(s) 1024 (e.g., pushing a prescribed physical or logical button, or articulating a prescribed voice command as to voice input controls), including via a device 924 that may be retained by the athlete (e.g., device 112 of FIG. 1); and/or (iv) performing (by the athlete or for the athlete, such as by an assistant) prescribed act(s), such act(s) being amenable for detection via image acquisition or data acquisition capabilities (e.g., exhibiting a prescribed body gesture for reception via the image acquisition capabilities, or issuing a prescribed gesture via sensors embedded in apparel, footwear, and/or accessories).

At step 1022, images may be acquired. As described herein, such images may be acquired variously. In example embodiments, generally, image acquisition is subject to parameters which may be configured so as to enable, enhance, optimize or otherwise provide for image processing for the purposes described herein. In example embodiments as described herein, images may be acquired via one or plural devices 924. As an example of plural devices 924, two devices are employed, wherein (i) such devices are calibrated for operation together (e.g., via known calibration approaches), so that (ii) one device 924 may acquire images associated with test start, and (iii) a second device 924 may acquire images associated with test completion. As another example employing two devices 924, both devices 924 may capture test start and/or test completion, whereby the images from each may be combined, in whole or in part, or otherwise, towards obtaining enhanced image processing and, thereby, enhanced assessments of initiation image and/or completion image (and/or, through shutter offsets, enhanced timing precision) and, in turn, enhanced test results and/or feedback.

At decision 1024, example embodiments may implement an "images retention" event test. At decision 1024, if an images retention event is or has been detected, image acquisition operations continue, and operations flow, e.g., to decision 1026. If such event is not or has not been detected, image acquisition operations continue, but example embodiments may implement an image discard process 1028.

In example embodiments, an images retention event may be implemented so as to enable acquisition of images in anticipation of upcoming test start for a performance test, while also providing, e.g., if test start is subject to delay, retention of a reasonable number of images (e.g., so as to preserve image storage space for relevant images). As an example, if image acquisition is proceeding, but the athlete has not yet entered the activity space, images retention may not be merited. As another example, if image acquisition is proceeding and the athlete has entered the activity space, but not progressing toward initiation of performance test conduct, images retention may not be merited. As another example, if images acquisition is proceeding and the athlete has not only entered the activity space, but also is progressing toward initiation of performance test conduct, images retention may be merited.

An images retention event may be variously implemented. In example embodiments, an images retention event may be implemented to be or to be associated with, as examples: (i) the athlete engaging (or having engaged by an assistant) prescribed input/control capabilities of device(s) 924 (e.g., pushing a prescribed physical or logical button, or articulating a prescribed voice command as to voice input controls), including via a device 924 that may be retained by the athlete (e.g., portable device 112 of FIG. 1); (ii) the athlete performing (or having performed by an assistant) prescribed act(s), such act(s) being amenable for detection via image acquisition or data acquisition capabilities (e.g., exhibiting a prescribed body gesture for reception via the image acquisition capabilities, or issuing a prescribed gesture via sensors embedded in apparel, footwear, and/or accessories); and/or (iii) the athlete preparing in the activity space to conduct a performance test, which conduct preparation may be amenable to detection by image acquisition capabilities.

As to conduct preparation as an images retention event, example embodiments may be implemented to detect any/selected such events via image processing. In configuring image processing for such detection, understood is that the athlete is preparing in the activity space and, as such, that acquired images may be anticipated to include object(s) corresponding to the athlete, and that at least such object(s) may exhibit motion(s) among images, e.g., from image to image in the sequence. With such understandings, an images retention event may be deemed to have occurred if, as an example, motion is detected that satisfies (e.g., meets, or exceeds) a selected images retention threshold. In this example approach, such detection may assess motion across a selected number of consecutive images in a sequence, or may be applied as to a selected number of non-consecutive images in a sequence, or otherwise.

As to the prescribed act(s), example embodiments may be implemented in which such act(s) include one or more components. As examples, such act(s) may be an "initial position" (as described hereinabove), or may be such "initial position" combined with preceding or subsequent athlete activity. To illustrate, an arrowhead agility exercise, as described herein, may include various constituents, and each constituent may include various components, such that, among other components serving as or to formulate prescribed act(s), such act may be either/both (i) a prescribed stance as an initial position and (ii) a prescribed period of motionlessness or substantial motionlessness in such stance prior to test start. As another illustration, a kneeling power ball chest launch exercise, as described herein, may include various constituents, and each constituent may include various components, such that, among other components serving as or to formulate prescribed act(s), such act may be either/both (i) a prescribed, kneeling stance as an initial position and (ii) a prescribed period of motionless or substantially motionless in such stance prior to test start.

For an images event retention test wherein selected component(s) serve to signal the event, example embodiments are implemented toward detecting such components and, upon such detection, enabling operations to proceed. In configuring image processing for such detection, understood is that the athlete is preparing in the activity space and, as such, that acquired images may be anticipated to include object(s) corresponding to the athlete and or equipment, and that at least such object(s) may exhibit motions among images, e.g., from image to image in the sequence. With such understandings and employing image processing, an images retention event may be deemed to have occurred if, as an example, motion of the sequence is detected to approach or pass a selected threshold (e.g., pass below a low threshold, as such motion value may follow from or be associated with the prescribed motionlessness associated with an "initial position"). Further to the above, an images retention event may be deemed to have occurred if, as an example, motion in the sequence is detected not only to approach or pass a selected threshold, but also to be sustained at or near, or otherwise within some range thereabout (e.g., for a time period relating to the prescribed period of athlete motionlessness in the "initial position"). In this example approach, such detection may be implemented in various ways, including, as examples, to assess motion across a selected number of consecutive images in a sequence, or may be applied as to a selected number of non-consecutive images in a sequence, or otherwise.

Example embodiments may be implemented to detect an images retention event via a combination of foregoing approaches. As an example, image processing may be employed in such embodiments to detect an images retention event when the motion of the sequence approaches or passes a selected threshold, including, e.g., with the qualification that such motion value is preceded and/or followed by a relatively higher or lower motion value.

In the foregoing example approaches, such detection may or may not be limited to detection of motion as to object(s) corresponding to the athlete and/or certain equipment (e.g., relevant motion may be that among frames as a whole). As such, images retention event detection may be implemented via image processing at a relatively high level (e.g., via frame differencing).

Under the circumstance wherein an images retention event is not detected, example embodiments may include an image discard process, which process may be variously implemented. As examples, an image discard process may discard (e.g., from image memory) images as follows: (i) discard all images acquired as of a configured step (e.g., that decision 1026 or a prior step, such as, e.g., ready event, at step 1014); (ii) discard a configured quantity of images (e.g., via a number of images, or as to a percentage of the total number of images, with such number or percentage being determined via various understandings, estimates or other factors, including, e.g., the acquisition frequency and typical time periods that may be associated with activities prefatory to performance test conduct); or (iii) discard a calculated number of images (e.g., based on image memory size, image acquisition time, image acquisition frequency, image resolution, number of imagers, estimated imaging durations, safety margins, etc.). In example embodiments, an image discard process discards images that precede images of potential relevance to an images retention event. In example embodiments, an image discard process protects images that are potentially relevant to detection of an images retention event, e.g., by not discarding at all, or by preserving in a buffer, e.g., for a configured time).

From the images retention event, operations flow to a "confirming" event test, at decision 1026. If a confirming event is or has been detected, image acquisition continues, and operations flow, e.g., to decision 1034. If such confirming event is not or has not been detected, image acquisition continues, and operations flow to a standby process, at decisions 1030, 1032.

In example embodiments, a standby process may be various implemented. An example standby process is depicted in FIG. 10, via decisions 1030 and 1032. At decision 1030, if a confirming event is not or has not been detected, a first time condition may be tested, which time condition may be implemented by comparing a timer to a first time period threshold (TP1). At decision 1032, if a confirming event is not or has not been detected, a second time condition may be tested, which time condition may be implemented by comparing a timer to a second time period threshold (TP2). The first and second time conditions may or may not share either or both the same timer and/or the same time period threshold. The first and/or second timer may be started (or re-started), as examples: (i) upon detection of the images retention event; (ii) upon initiation of image acquisition for the performance test; or (ii) upon some other event or via some other configuration (e.g., trigger, cue, etc.). The first timer may be started concurrently with one of the foregoing, while the second timer may be started with the same or another. The time period thresholds TP1 and TP2 may be variously configured, including responsive to one or more of: the available image memory, the image acquisition frequency, the image resolution, the anticipated time duration for conducting the performance test, and/or other parameters/conditions. In example embodiments, TP2 is greater than TP1.

In the example standby process depicted in FIG. 10, at decision 1030, if the first timer fails to satisfy (e.g., meet or exceed) the first time period threshold TP1, operations return to the confirming event of decision 1026. At decision 1030, if the first timer satisfies TP1, operations flow to decision 1032. At decision 1032, if the second timer fails to satisfy (e.g., meet or exceed) the second time period threshold TP2, operations flow: to the image discard process, at step 1028 and, from the image discard process, to the acquire images process, at step 1022, and then to the images retention event test, at decision 1024. As such, if the first timer satisfies TP1 without the second timer satisfying TP2, images may be discarded. Moreover, the previously-detected existing images retention event becomes ineffective (i.e., as if that images retention event had not been detected), such that the images retention event test is renewed. At decision 1032, if the second timer satisfies the second time period threshold TP2, operations end.

In example embodiments, a confirming event may be implemented so as to enable continued acquisition of images in anticipation of imminent athlete initiation of a performance test, while also providing e.g., if such initiation is subject to delay, retention of a reasonable number of images (e.g., so as to preserve image storage space for relevant images). In example embodiments, a confirming event follows an images retention event, which images retention event may be detected, as previously described, via image processing directed to detecting, e.g., athlete activity prefatory to performance test conduct. However, after detection of an images retention event based, the athlete may or may not initiate the performance test, whether at all or timely. Accordingly, in example embodiments, a confirming event may be implemented, such as to enforce a level of discipline as to operations, including as to the athlete.

A confirming event may be variously implemented. In example embodiments, a confirming event may be implemented to be, or to be associated with, as examples: (i) the athlete engaging (or having engaged by an assistant) prescribed input/control capabilities of device(s) 924 (e.g., pushing a prescribed physical or logical button, or articulating a prescribed voice command as to voice input controls), including via a device 924 that may be retained by the athlete (e.g., portable device 112 of FIG. 1); (ii) the athlete performing (or having performed by an assistant) prescribed act(s), such act(s) being amenable for detection via image acquisition or data acquisition capabilities (e.g., exhibiting a prescribed body gesture for reception via the image acquisition capabilities, or issuing a prescribed gesture via sensors embedded in apparel, footwear, and/or accessories); (iii) the athlete preparing in the activity space to conduct a performance test; (iv) the athlete initiating conduct of a performance test (e.g., a "test start", as described herein) or otherwise conducting a performance test; and/or (v) a combination of one or more of these.

The descriptions herein respecting image processing to detect an images retention event inform image processing for detecting a confirming event. In image processing to detect a confirming event, it is understood not only that the athlete is present in, and at least at times moving in, the activity space, but also that the athlete may imminently initiate, or have initiated, performance test conduct, e.g., test start. As such, acquired images may be anticipated to include object(s) corresponding to the athlete, which object(s) exhibit motions among images in imaging sequence. With such understandings, a confirming event may be deemed to have occurred if, as an example, motion in the imaging sequence is detected that satisfies (e.g., meets or exceeds) a selected confirming event threshold. In example embodiments, such confirming event threshold may be greater than the images retention event threshold, which greater value is congruent with detection that may include test start, rather than initial position/motionlessness (e.g., greater athlete movement tends to correspond to greater object motion in the imaging of that movement).

As to the athlete performing prescribed act(s) as a confirming event, example embodiments may be implemented in which the prescribed act(s) are or are formulated using one or more components. In example embodiments, such act(s) may include, e.g.: "test start"; other component(s) implicating athlete movement; "initial position" (as previously described); or combinations of one or more of these. So employing any such components in formulating such act(s), example embodiments may be implemented to detect a confirming event via image processing, including, e.g., image processing informed by the descriptions as to detecting an images retention event.

If a confirming event is identified via image processing's detection of a test start, such detection may, in effect, identify a specific image of the imaging sequence that corresponds to the athlete's initiation of the performance test (such specific image sometimes referred to herein as an "initiation image"). Similarly, such confirming event detection may result from means other than image processing (e.g., via data acquisition, communication and/or processing capabilities, of or among devices(s) 924 and/or sensors), which detection may tag a specific image, such specific image having been acquired at a time corresponding to such detection. Moreover, such confirming event detection may result from a combination of such means with the image processing detection. Such specific image(s) may, in some circumstances, be one of two images that bracket the initiation image (e.g., if the image data indicates that the athlete's initiation of the performance test occurred between two consecutive images in the imaging sequence), such that the initiation image may be resolved via interpolation of two images. In example embodiments, such specific image(s) may be treated as placeholder(s) for further image processing toward concluding on an initiation image, e.g. further image processing employing more powerful processing methods in order to determine the initiation image.

In some example embodiments, an images retention event test, as in decision 1024, may be omitted in favor of, or may otherwise be combined in, a confirming event test, as in decision 1026.

From the confirming event test, operations may flow to a termination event test, at decision 1034. If a termination event is or has been detected, operations may flow to the terminate acquired images process, at step 1036. In example embodiments, if a termination event is not or has not been detected, image acquisition continues and will continue until a termination event is detected. In other example embodiments, if a termination event is not or has not been detected, operations may be implemented to flow to a standby process (not shown). Any termination event standby process may be structured the same as, or similar, to the confirming event standby process shown at decisions 1030 and 1032. As an example, a termination event standby process may be implemented based on a max time period threshold (e.g., a time during which the test should be completed, such time period being configured from a priori knowledge of the performance test and/or from a universe of historical data assembled from athletes having (properly) conducted such test). In such example, the termination event standby process includes a timer that is compared to the max time period threshold, such that, if no termination event is or has been detected when the timer satisfies the threshold, operations flow to the terminate acquired images process, at step 1036.

In example embodiments, a termination event may be implemented so as to enable discontinuation of image acquisition so that unnecessary or irrelevant images are not acquired. In example embodiments, image acquisition may be terminated following the athlete's completion of the test.

A termination event may be variously implemented. In example embodiments, a termination event may be implemented to be, or to be associated with, as examples: (i) the athlete engaging (or having engaged by an assistant) prescribed input/control capabilities of device(s) 1024 (e.g., pushing a prescribed physical or logical button, or articulating a prescribed voice command as to voice input controls), including via a device 1024 that may be retained by the athlete (e.g., portable device 112 of FIG. 1); (ii) the athlete performing (or having performed by an assistant) prescribed act(s), such act(s) being amenable for detection via image acquisition or data acquisition capabilities (e.g., exhibiting a prescribed body gesture for reception via the image acquisition capabilities, or issuing a prescribed gesture via sensors embedded in apparel, footwear, and/or accessories); (iii) the athlete or equipment, or both, reaching or passing prescribed location(s) in or as to the activity space (e.g., relative to one or more test elements), as determined via data acquired from sensors embedded in the equipment, in the athlete's apparel, footwear, and/or accessories, or in a device 1024 carried on the athlete, including in combination(s) thereof, and/or in combination(s) with other devices 1024 and/or with other sensors, transceivers or other electronic devices, within the athlete's instant BAN, PAN, or LAN, such location(s) being determined via any of various means, including GPS, AGPS, signaling, signal strength measures, or otherwise; (iv) the athlete completing conduct, or otherwise causing completion, of a performance test via, e.g., the athlete's completion of a component, the athlete's interaction with a test element (e.g., crossing a finish line) or a test element—acted on by the athlete—achieving a prescribed state change (e.g., an athlete-thrown ball transitioning from flight to landing), as described herein (e.g., such completion sometimes referred to herein by the term "test completion", as previously described); (v) the athlete physically departing the activity space, or remaining in the activity space, but with no physical activity relevant to the performance test; and/or (vi) a combination of one or more of these.

The descriptions herein respecting image processing to detect an images retention event and/or a confirming event inform image processing for detecting a termination event. In image processing to detect a termination event, it is understood not only (i) that the athlete has been present in, and at least at times has been physically moving in, the activity space, but also (ii) that the athlete will complete conduct of the performance test, or that the test will otherwise be completed (e.g., test completion) and, in turn, that the athlete's physical movement within the activity space may decline or end (e.g., at least as to the test). As well, the nature of the performance test is known, including any equipment employed (including its size, shape, anticipated location(s)), any relevant interactions between the athlete and the equipment (and the relative timing within the test) and anticipated state changes as to the equipment (e.g., including movements thereof, and changes in or termination of such movement(s)). As such, acquired images may be anticipated to include object(s) corresponding to the athlete and/or the equipment, at least some of which object(s) will exhibit motion(s) among images, e.g., from image to image in the sequence. With such understandings, a termination event may be deemed to have occurred, as an example, if objects and objects' motion(s) are detected which correspond to athlete activity and/or equipment activity that is consistent with completion of the performance test. Examples include image processing may detect, e.g.: (i) a test completion (e.g., the athlete having crossed the start-stop line 1008, such as, e.g., any body part crossing a vertical plane associated with the cone(s) physically demarcating such line 1008, whether such lens is positioned on such line or remote therefrom and/or at an angle thereto; (ii) an athlete activity directed to departure from the activity space, or to movement into and/or loitering in the periphery of the activity space, including an absence or substantial absence thereof (e.g., any of which alone or together may indicate that the athlete has ceased or substantially ceased movement and/or conduct of the test); (iii) and/or, a (final) state change for equipment (e.g., as anticipated for the test as to known equipment).

If a termination event is identified via image processing's detection of a test completion, such detection may, in effect, identify a specific image of the imaging sequence that corresponds to the end point of the performance test (such specific image sometimes referred to herein as a "completion image"). Similarly, such termination event detection may result from means other than image processing (e.g., via data acquisition, communication and/or processing capabilities, of or among devices(s) 924 and/or sensors), which detection may tag a specific image, such specific image having been acquired at a time corresponding to such detection. Moreover, such termination event detection may result from a combination of such means with the image processing detection. Such specific image(s) may, in some circumstances, be one of two images that bracket the completion image (e.g., if the image data indicates that the athlete's completion of the performance test occurred between two consecutive images in the imaging sequence), such that the completion image may be resolved via interpolation of two images. In example embodiments, such specific image(s) may, as previously stated respecting an initiation image, be treated as placeholder(s) for further image processing toward concluding on a completion image, e.g. further image processing employing more powerful processing methods in order to determine the completion image.

Responsive to detection of a termination event at decision 1034 (or to a termination event standby process), operations flow to a terminate acquired images process, at step 1036. In the terminate acquired images process, image acquisition is terminated. Such termination may be variously implemented. In example embodiments, such termination may be effected upon the detection of the termination event. In other example embodiments, such termination may be effected after a configured time period has passed from detection of the termination event (e.g., toward recording additional images relevant or that may be relevant to image processing). Such configured time period may respond to various understandings, estimates or other factors, including, e.g.: time periods associated with the performance test; image memory size; image acquisition frequency; image resolution; number of imagers; safety margins, etc.).

From termination of image acquisition at step 1036, operations flow to decision 1038, in which a determination is made whether to submit the acquired images to image processing. If the determination at step 1038 is not to so submit, operations flow to step 1044, at which step operations may be (i) re-started so as to proceed with further performance testing (e.g., to repeat the current performance test for the test's prescribed number of repetitions, or to advance to the next performance test in the battery of tests in which the current performance test resides, or to select a new battery of tests or an individual test), or (ii) ended. If the determination at step 1038 is to submit for image processing, operations flow to image processing at step 1040, and from imaging processing to a test results/feedback process at step 1042.

At step 1040, image processing may be performed. In example embodiments, image processing may be implemented as to image data associated with constituent(s), including various components thereof. In example embodiments, as described herein, image processing may be implemented to detect images associated with one or more of test start, test milestone(s), and/or test completion. As described herein, image processing may yield: an initiation image corresponding to test start; a completion image corresponding to test completion; and/or a milestone image corresponding to each respective test milestone. As described herein, image processing may yield more than one image corresponding to any one or more of test start, test completion and/or a test milestone. That is, image processing may, in some circumstances, yield two images that bracket the physical event, e.g., if the image data indicates that the physical event occurred between two consecutive images in the imaging sequence), in which case, image processing may yield an interpolated image, i.e., an image that resolves the two images.

In example embodiments, image processing may be performed iteratively. As an example, image processing may be implemented so as to be performed in phases among all objects and the object(s) corresponding to the athlete: (i) in a first phase, image processing may analyze as to motion(s) corresponding to all or substantially all physical movement captured in the imaging (e.g., overall motion present in the image data among frames in an image sequence); and (ii) in a second phase, image processing may analyze as to motion(s) corresponding to overall movement of the athlete's body. As another example, image processing may be implemented so as to be performed in phases among the object(s) corresponding to the athlete: (i) in a first phase, image processing may analyze as to motion(s) corresponding to overall movement of the athlete's body and (ii) in a second phase, image processing may analyze as to motion(s) corresponding to movement or relative movement of/among the athlete's head, torso, arms, legs, etc. In either of these foregoing examples, the objects and motions corresponding to the athlete's body, body parts and body movements may be implemented so that such objects and motions are analyzed in combination(s), such as aggregate motion or relative motion, including relative to an object corresponding to test element(s) (e.g., a club, a ball or a start/stop line). As another example, image processing may be implemented so as to be performed in phases among the object(s) corresponding to the athlete, as well as the object(s) corresponding to one or more test elements (e.g., a golf club and a golf ball): (i) in a first phase, image processing may analyze as to motion(s) corresponding to overall movement of the athlete's body and the equipment, (ii) in a second phase, image processing may analyze as to motion(s) corresponding to movement or relative movement of/among the athlete's head, torso, arms, legs, etc., and relative movement of the one piece of equipment (e.g., a golf club), such as with respect to one or more of such athlete's body part(s), and (iii) in a third phase, image processing may analyze as to motion(s) corresponding to movement/change in state as to another piece of equipment (e.g., as to the golf ball's flight and landing), such as with respect to yet other test element(s) (e.g., yardage and/or directional indicator(s)). As to either of these approaches, image processing may be implemented to address aberrant motion, such as that associated with physical movement of the device's imaging acquisitions capabilities, particularly the device's imaging chip.

In example embodiments, image processing at step 1040 may be implemented so as to be initiated during image acquisition. In such embodiments, such image processing may execute concurrently, or in coordination, with other processes. In such embodiments, for example, image processing may be employed in earlier steps, such as for the confirming event test at decision 1026, toward detecting the initiation image thereat, and such as for the termination event test at decision 1034, toward detecting the completion image thereat. As described herein, such confirming event test at decision 1026 and such termination event test at decision 1034 may identify placeholder images as to an initiation image and/or a termination image, including for further image processing. In such case, such further image processing may be initiated concurrently with or following such tests, with or without any the termination of image acquisition at step 1036. Moreover, such further image processing may employ more powerful processing methods.

Image processing at step 1040 may be implemented to admit input from the athlete. As an example, image processing may be implemented via portable electronic device(s) 924, including in connection with a mobile application. Such device executing such mobile application may provide a user interface experience by which the athlete (or an assistant) engages the device's input/control capabilities (e.g., pushing a prescribed physical or logical button, or articulating a prescribed voice command as to voice input controls), so as to provide such input. As an example, via such user interface experience, the athlete may be engaged to review all or part of an image sequence associated with the athlete's constituent conduct, so as to, e.g.: (i) identify irrelevant portions of the imaging, e.g., prefatory and/or post-completion activities, (ii) associate one or more candidate images with one or more of test start, test completion, and/or test milestone(s) (e.g., the athlete selects a frame which the athlete considers to display an image corresponding to the athlete's initiation or completion of the performance test or of any test milestone thereof, and/or (iii) identify object(s) in the image (e.g., via a touch-sensitive display, the athlete may select or circumscribe a piece of equipment and/or the athlete's body or selected body parts, any one or more of which identifications may enhance image processing founded on such object(s)). Toward so engaging the athlete, the user interface experience may display queries, requests, instructions, guidance or other feedforward so as to direct proper/timely input from the athlete.

In example embodiments, image processing at step 1040 may yield outputs that are provided to the test results/feedback process, at step 1042. Such outputs may include any one or more of the initiation, completion and milestone images (e.g., for display to the athlete or others). Such outputs may also include data that enables measurements, including in format and content, appropriate to measurements provided via the test results/feedback process, at step 1042. As an example, such output data may include the frame numbers, frame times, or other frame addressing, any of which may be absolute or against a reference. Such output data may also be provided together with the image acquisition frequency, any time offsets (e.g., shutter offset among plural imagers), or the like. Such output data, via format and content, enables, e.g., the measure of time differences, which time differences may be test results or may enable calculation of test results. As an example, for the arrowhead agility exercise, the image processing output may include the initiation image, the completion image and the image acquisition frequency in frames per second, with the initiation image denoted as frame #F1, the completion image denoted by frame #F2 and the image acquisition frequency denoted as FPS, such that measurement of the elapsed time for the test is the (#F2-#F1)/FPS. In such case, if #FP1=0, #FP2=3000, and FPS=50 fps, the measurement is (3000-0)/50=60 seconds. As another example, for the power ball chest launch exercise, similar outputs may be provided, with the measurement yielding an elapsed time capturing the ball's flight, which elapsed time, together with the balls known weight and the athlete's known profile (height, etc.), may be applied to a predetermined ballistics formula toward measuring distance of the ball's flight.

In certain further descriptive embodiments, aspects of this disclosure involve obtaining, storing, and/or processing athletic data relating to the physical movements of an athlete. The movements may be part of one or more activities. An activity, as such term may be used herein, may include, as an example, golf. A constituent, as such term is used herein, may include, as an example, a swing of a golf driver (hereafter, sometimes referred to as a "swing"). Components of a golf driver swing are known and some of which are described herein. In other example activities, a constituent may also be a swing, but of other, relevant equipment. A constituent is a movement that may include one or more components. A constituent, and each component, has physical characteristics, including, e.g., various velocities, accelerations, rotations, durations, etc. In example embodiments, a constituent (which may be equivalent to a feature disclosed above), e.g. a swing, may be captured in image data (e.g., images in sequence or video) via one or more image acquisition devices (hereafter, each such device may be referred to as a "camera"). A camera may be provided in a smart phone, such as an HTC One X+. In capturing the swing, the image data captures movement of the user's body and body parts, as well as equipment, such as a golf club. The body, body parts and equipment may be captured in the image data as objects. The movements of the swing (and/or any objects in the image data) are captured in the image data as motion. Components of the swing are captured in the image data as swing features. For example, at any given time, more than one component may occur (e.g., body part movement and club movement), such that more than one swing feature may occur.

Imaging of the activity, movement or its constituents, such as of a swing, its components, and the velocities, accelerations, rotations thereof may be referenced with respect to one or more selected axes (e.g., in the image, a coordinate system and/or axes of rotations may be provided) and/or reference point(s). Imaging may also be variously timed, including absolute (chronography) or relative to the shutter of an image-capturing device (e.g., fps).

Using a golf swing as one example, not all components, features, etc. may be relevant for the purposes of various embodiments. A component's relevance may be responsive to, among other things, a relationship to swing results (e.g., changes in the component may have large, medium or small impact on the distance or accuracy for a golf ball's flight); the complexity of its movement (including as to velocities, accelerations, rotations and any other of its characteristics); and/or challenges associated with imaging or analysis of such component/feature. The imaging and imaging analysis challenges may be related to, e.g.: the available computing power (e.g., local, distributed, and time based); resource (energy) consumption issues; imaging issues (e.g., resolution, fps, etc.). A component may be relevant because such component is present in plural swings, e.g., in the various swings associated with the golf clubs found in a typical user's bag, and/or among swings of different sports. As such, image data associated with irrelevant components may not be analyzed. Moreover, swing features may or may not be contiguous in the image data sequence. As to any selected swing feature in the image data sequence, the may be: simultaneous with one or more other swing features (i.e., appear in the exact same images or video frames); overlapping with others (i.e., appear in some but not all images or video frames); contiguous with others (i.e., the selected feature's last frame is the frame just before the other feature's first frame); or isolated from all other features. All swing features, together, may include all relevant image data associated with the captured swing imaging.

One or more components of a constituent may not be relevant in effecting various embodiments, or may not be relevant throughout. As such, these components may either (i) not ever part of the analysis or (ii) not always part of the analysis (e.g., the component may be relevant in some cases, such as, being a back-up data source if another component cannot be imaged). Relevance may be based on the complexity and/or resource demands of that component's analysis. Relevance may be determined based on diminishing returns from its analysis. Relevance may be based on other factors, or combinations of any of these. As to diminishing returns in a golf swing, for example, the user's trunk rotation (angular velocity and/or range) may be relatively important at one time (thus, analyzed in the image domain, including perhaps to the exclusion of one or more other components), and may be relatively unimportant at another time (thus, perhaps excluded from the analysis that now focuses on one or more other components, including, e.g., one or more of the previously-excluded components).

Analysis may be of the image data overall, swing feature-by-swing feature, or as a sequence of swing feature data. As per above, image data may be analyzed in combination with or otherwise responsive to other data, such as sensor data and/or swing result data. Analysis outputs are input, alone or together with other input (e.g., other input may be results data, user input or otherwise), to a feedback generator function. The feedback generator function may be provided as part of one or more computer-implemented instructions on a non-transitory computer-readable medium, including those described herein, and/or may be provided as a service (e.g., a web-service, or otherwise), or some combination. The feedback generator generates feedback signal(s), which feedback signals are provided to the user. The feedback signal(s) may be variously so provided, including, as examples, through additional hardware and/or software functions, or one or more transducers, or a combination. Examples, include using the HTC One X+'s native functions, e.g., the HTC One X+'s speakers and/or camera LEDs.

We claim:

1. A computer-implemented method for providing audible feedback to an athlete during performance of a physical activity comprising:
    receiving at a computer in real-time, a plurality of sequential images during a first athlete's performance of an physical activity;
    processing by the computer in real-time using an optical flow process, pixels from the plurality of sequential images to identify image data of the first athlete performing a first feature of a first athletic movement involving a sporting device during the physical activity;
    in response to identifying the performance of the first feature, outputting a real-time first audio feedback signal having a first audible tone having a first ADSR envelope based upon the movement properties of the sporting device during the first feature;
    detecting, as part of the real-time processing of pixels from the plurality of sequential images, image data within the plurality of images indicative that the first athlete is performing a second feature of the first athletic movement;
    outputting, in real-time, a second audio feedback signal having a second tone having a second ADSR envelope based upon the movement properties of the sporting device during the second feature such that the athlete receives audio feedback during performance of the athletic movement configured to provide audible tempo feedback in regards to the athlete's performance of the first and second features of the athletic activity, where the audible tempo feedback is based on prior recorded movement properties of the sporting device associated with the first athlete; and,
    calculating an athletic score based on the athlete's performance of the first and second features of the athletic activity.

2. The method of claim 1, wherein the first audio feedback signal is a first audible tone at a first frequency and generating the second audio feedback signal comprises modulating the audible tone to a second frequency.

3. The method of claim 1, wherein the identification of the first feature comprises identifying an initiation image comprising:
    identifying pixels that correspond to at least one of a specific first body portion or sporting device, wherein the first body portion or sporting device is selected based upon a predetermined physical activity the athlete is to perform; and
    determining, based upon the identified pixels, whether the pixel data is altered between a plurality of images within the sequential images such that the alteration satisfies a first threshold.

4. The method of claim 1, wherein an output of the optical flow process is provided as an input to a motion entropy determination process comprising:
    providing flow field data comprising a pixel-distance change of an identified object from a first image to a second image; and
    using the flow field data to identify a specific type of motion of the athlete represented in the image data during performance of the physical activity.

5. The method of claim 4, wherein the second feature is detected from a motion parameter based on at least one of a velocity value, an acceleration value, a location of a body portion of the athlete, or a location of a sporting device within the image data.

6. The method of claim 5, wherein the motion parameter is determined based upon, at least in part, determining that a velocity value or an acceleration value meets a first threshold.

7. The method of claim 5, further comprising:
    utilizing the motion parameter in the generation of the second audio feedback signal.

8. The method of claim 4, wherein the physical activity is a golf swing having an upswing athletic movement and a subsequent downswing athletic movement; and wherein detecting the image data that the first athlete is performing the first feature comprises detecting pixel data indicative that a golf club is within a first distance from a ground surface and detecting the image data that the second athlete is performing the second feature of the upswing athletic movement is detected from pixel data indicative that the golf club is within a second distance from a ground surface.

9. The method of claim 2, further comprising:
    based upon the detection of at least one of the first and the second feature, transmitting a third audible feedback signal having a third audible tone having a third ADSR envelope at a predetermined time based upon the occurrence of the first or second feature configured to indicate the proper timing for the athlete to perform an additional feature of the athletic performance.

10. A computer-implemented method for determining an athletic attribute of an athlete comprising:
    receiving a plurality of sequential images, wherein at least a first image comprises image data of an athlete before initiating performance of a predetermined physical activity and a plurality of subsequent images comprise image data of the athlete performing the predetermined physical activity;
    processing using an optical flow process at least a portion of the plurality of subsequent images to identify a first range of images located after the first image, wherein the identification is based upon pixel data for a threshold quantity of pixels in the subsequent images reaching a first threshold level indicative that movement of an object in the images has occurred;

processing the image data to locate an object having a known dimension, and using the known dimension to calibrate the image data;

processing images within the first range of images to identify an initiation image of a first feature involving a sporting device of the physical activity, comprising:

identifying pixels in the first range of images that correspond to a specific first body portion of the athlete, wherein the first body portion is selected based upon the predetermined physical activity;

determining, based upon the identified pixels, whether the pixel data is altered such that alteration satisfies a first body portion movement quality threshold; and utilizing the initiation image and the determination of the first body portion movement quality threshold in a determination that the athlete performed the first feature;

in response to identifying the performance of the first feature, transmitting a real-time first audio feedback signal having a first audible tone having a first ADSR envelope based upon movement properties of the sporting device during the first feature, where the first audible tone is configured to provide audible tempo feedback for the athlete's performance of the first feature based on prior recorded movement properties of the sporting device or the first athlete; and calculate an athletic score based on the movement properties of the sporting device during the first feature.

11. The method of claim 10, further comprising:

processing at least a portion of the plurality of sequential images to locate a completion image sequentially located after the first image, the completion image comprising image data of the athlete immediately upon completing the first feature of the predetermined physical activity.

12. The method of claim 11, further comprising:

calculating a physical activity duration based upon the located initiation image and the located end image.

13. The method of claim 12, wherein the output of the optical flow process is provided as an input to a motion entropy determination process comprising:

providing flow field data comprising a pixel-distance change of an identified object from a first image to a second image; and using the flow field data to identify a specific type of motion of the athlete represented in the image data during performance of the predetermined physical activity.

14. The method of claim 10, further comprising:

detecting, as part of the real-time processing, image data within the plurality of images indicative that the first athlete is performing a second feature of a first athletic movement; and outputting, in real-time, a second audio feedback signal having a second audible tone having a second ADSR envelope based upon the movement properties of the second feature such that the athlete receives audio feedback during performance of the athletic movement configured to provide audible tempo feedback in regards to the athlete's performance of the first and second features of the athletic activity.

15. The method of claim 14, wherein the first audio feedback signal is a first audible tone at a first frequency and generating the second audio feedback signal comprises modulating the audible tone to a second frequency.

16. The method of claim 10, wherein the identification of the first feature comprises identifying an initiation image comprising:

identifying pixels that correspond to at least one of a specific first body portion or sporting device, wherein the first body portion or sporting device is selected based upon a predetermined physical activity the athlete is to perform; and determining, based upon the identified pixels, whether the pixel data is altered between a plurality of images within the sequential images such that the alteration satisfies a first threshold.

17. The method of claim 14, wherein the second feature is detected from a motion parameter based on at least one of a velocity value, an acceleration value, a location of a body portion of the athlete, or a location of a sporting device within the image data.

18. The method of claim 17, wherein the motion parameter is determined based upon, at least in part, determining that a velocity value or an acceleration value meets a first threshold.

* * * * *